(12) United States Patent
Hellmuth et al.

(10) Patent No.: US 7,868,185 B2
(45) Date of Patent: Jan. 11, 2011

(54) SHP-2 INHIBITORS AND PHARMACEUTICAL COMPOSITIONS COMPRISING THEM

(75) Inventors: Klaus Hellmuth, Berlin (DE); Walter Birchmeier, Schwanebeck (DE); Joerg Rademann, Berlin (DE); Stefanie Grosskopf, Berlin (DE)

(73) Assignees: Max-Delbruck-Centrum fur Molekulare Medizin, Berlin (DE); Forschungsverbund Berlin E, V., Berlin (DE)

(*) Notice: Subject to any disclaimer, the term of this patent is extended or adjusted under 35 U.S.C. 154(b) by 315 days.

(21) Appl. No.: 11/916,111

(22) PCT Filed: Jun. 1, 2006

(86) PCT No.: PCT/EP2006/062852
§ 371 (c)(1),
(2), (4) Date: Nov. 30, 2007

(87) PCT Pub. No.: WO2006/128909
PCT Pub. Date: Dec. 7, 2006

(65) Prior Publication Data
US 2008/0194563 A1    Aug. 14, 2008

(30) Foreign Application Priority Data
Jun. 1, 2005    (EP)    ................... 05090160

(51) Int. Cl.
C07D 231/08 (2006.01)
A01N 43/56 (2006.01)
(52) U.S. Cl. .................... 548/371.1; 514/404
(58) Field of Classification Search ............. 548/371.1; 514/404
See application file for complete search history.

(56) References Cited

OTHER PUBLICATIONS

Vippagunta et al.; "Crystalline solids"; 2001; Advanced Drug Delivery Reviews; 2-26.*
Hu, Yunan, et al.; "Identification of Selective Inhibitors for the Glycosyltransferase MurG via High-Throughput Screening"; Chemistry & Biology; 2004; pp. 703-711; vol. 11, No. 5, XP002348827.

(Continued)

*Primary Examiner*—Sreenivasan Padmanabhan
*Assistant Examiner*—Timothy P Thomas
(74) *Attorney, Agent, or Firm*—Millen, White, Zelano & Branigan, P.C.

(57) ABSTRACT

The present invention relates to small molecule protein tyrosine phosphatase inhibitors, especially Shp-2 inhibitors, of formula (I) and/or (II), and to pharmaceutical compositions comprising them. The invention is also directed to the use of said compounds for the treatment of phosphatase-mediated diseases, especially cancer and metastasis. The invention further concerns a method for treating a proliferative disease, a genetic disorder, an autoimmune disease, an angiogenic disorder or cancer in a patient in need of such treatment, comprising administering to said patient a therapeutically effective amount of at least one compound of formula (I) and/or (II).

18 Claims, 7 Drawing Sheets

Structure Activity Relationship of Compounds of Formula I

| Compound ID | R | X | IC50 Shp2 [µM] | Inhib. Scatt. |
|---|---|---|---|---|
| I-1 | (ethoxy-phenyl-NH-C(O)-propyl) | H | 2,2 | +++ |
| I-2 | (phenyl-CH2-) | Br | 4,9 | + |
| I-3 | (HO-CH(CH3)-C(O)-) | Br | 120 | - |
| I-4 | (allyl) | Br | >250 | - |

Compounds I-3 and I-4 are comparative compounds.

OTHER PUBLICATIONS

Wimmers, Erin, et al.; "Design and synthesis of inhibitors of the protein tyrosine phosphatase, SHP-2"; Peptides for the New Millennium; 2000; pp. 604-605; Kluwer Academic Publishers, XP009055304.

Database Chemcats Online Chemical Abstracts Service, Columbus, Ohio, US, Jan. 1, 2004, "Ambinter Screening Library", XP002349814.

Database Chemcats Online Chemical Abstracts Service, Columbus, Ohio, US, Sep. 17, 2004, XP002349815.

Database Chemcats Online Chemical Abstracts Service, Columbus, Ohio, US, Mar. 17, 2004, "Synthetic and Natural Compounds Product List", XP002349816.

Database Chemcats Online Chemical Abstracts Service, Columbus, Ohio, US, Apr. 25, 2003, "ChemDiv, Inc. Product Library", XP002349817.

Database Chemcats Online Chemical Abstracts Service, Columbus, Ohio, US, Jan. 18, 2005, "Interchim Intermediates", XP002349818.

Hu, Yunan, et al.; "Identification of Selective Inhibitors for the Glycosyltransferase MurG via High-Throughput Screening"; Chemistry & Biology; 2004; pp. 703-711; vol. 11, No. 5.

Wimmers, Erin, et al.; "Design and synthesis of inhibitors of the protein tyrosine phosphatase, SHP-2"; Peptides for the New Millennium; 2000; pp. 604-605; Kluwer Academic Publishers.

* cited by examiner

Fig. 1: Structure Activity Relationship of Compounds of Formula I
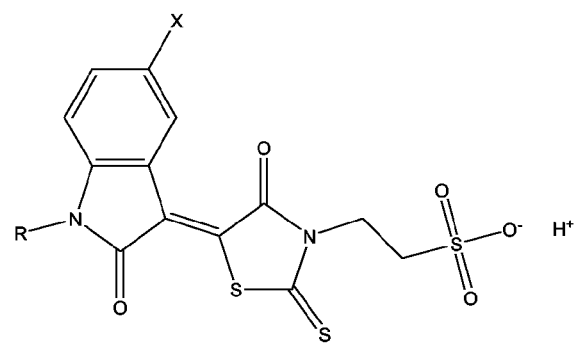
| Compound ID | R | X | IC50 Shp2 [µM] | Inhib. Scatt. |
|---|---|---|---|---|
| I-1 | 4-ethoxyphenyl-NH-C(O)-ethyl | H | 2,2 | +++ |
| I-2 | 4-ethylbenzyl | Br | 4,9 | + |
| I-3 | -CH(CH₂CH₃)-C(O)OH | Br | 120 | - |
| I-4 | allyl/but-2-enyl | Br | >250 | - |
Compounds I-3 and I-4 are comparative compounds.

Fig. 2: Structure Activity Relationship of Compounds of Formula II

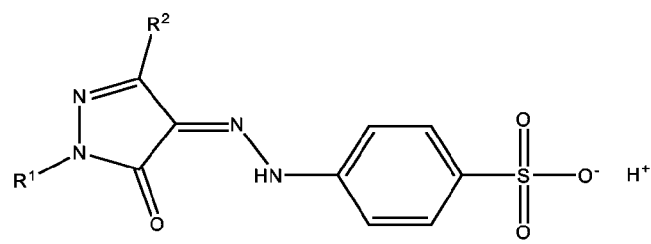

| Compound ID | R¹ | R² | IC50 Shp2 [µM] | Inhib. Scatt. at 15 µM |
|---|---|---|---|---|
| II-1 | phenyl | 4-O₂N-phenyl | 4.8 | +++ |
| II-2 | 4-phenyl-thiazol-2-yl | phenyl | 19 | − |
| II-3 | phenyl | phenyl | 36 | + |
| II-4 | H₂N-C(=S)− | 4-O₂N-phenyl | >250 | − |
| II-5 | 4-phenyl-thiazol-2-yl | H₃C− | >250 | − |
| II-6 | phenyl | 4-F-phenyl | 79 | − |
| II-7 | phenyl | 3-O₂N-phenyl | 24 | − |
| II-8 | 4-F₃C-phenyl | 4-O₂N-phenyl | 3.4 | ++ |
| II-9 | phenyl | 4-Cl-phenyl | 34 | − |
| II-10 | 4-EtOOC-phenyl | 4-O₂N-phenyl | 3.3 | +++ |
| II-11 | 4-F-phenyl | 4-O₂N-phenyl | 6.6 | +++ |
| II-12 | 4-HOOC-phenyl | 4-O₂N-phenyl | 14 | + |

Compounds II-4 and II-5 are comparative compounds.

Fig. 3: HGF/SF Scattering Assay with Compounds I-1 and II-1
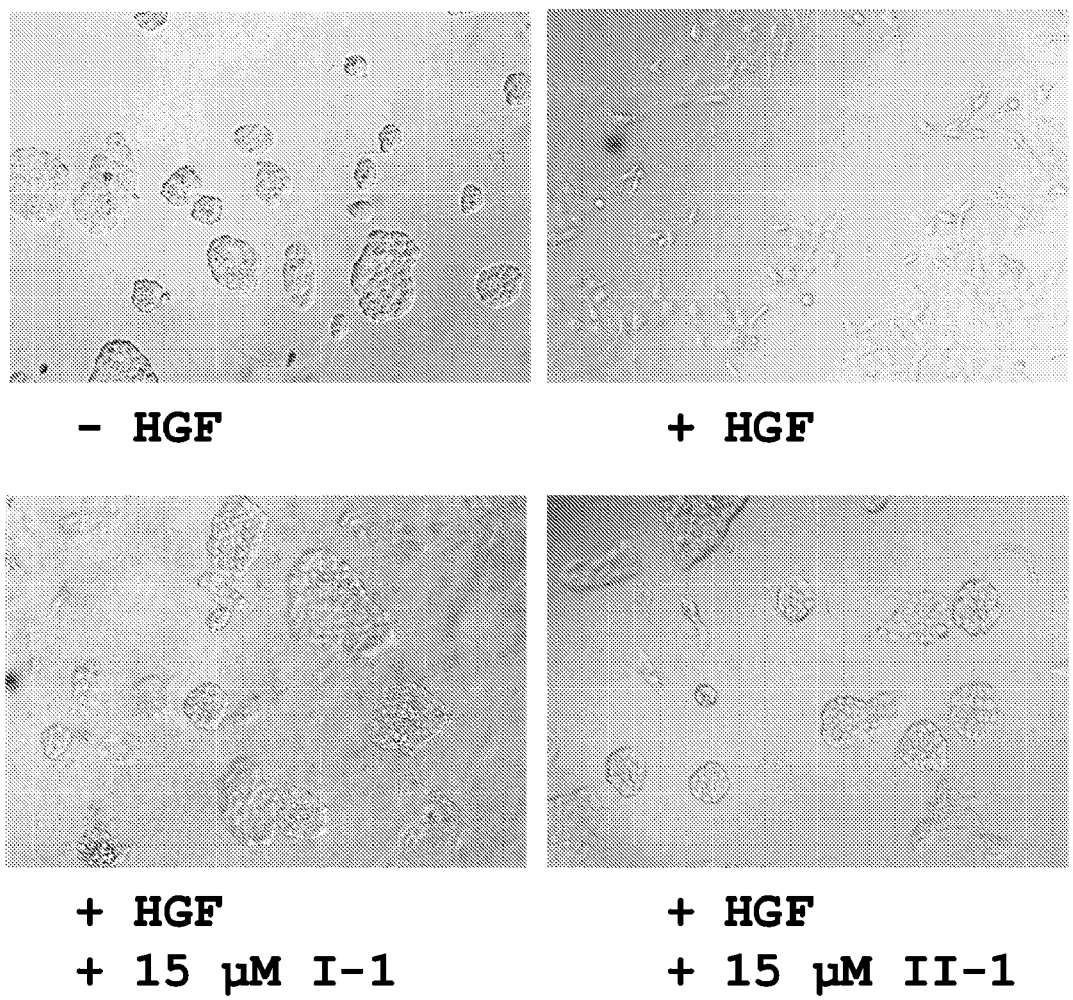

Fig. 4: HGF/SF Phosphorylation Assay with Compound II-1
A
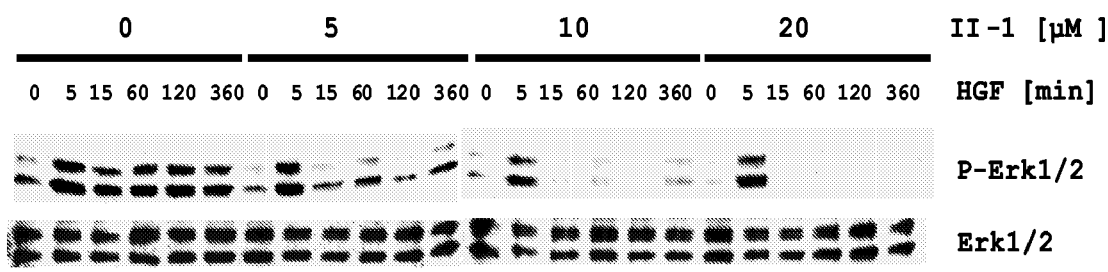
B
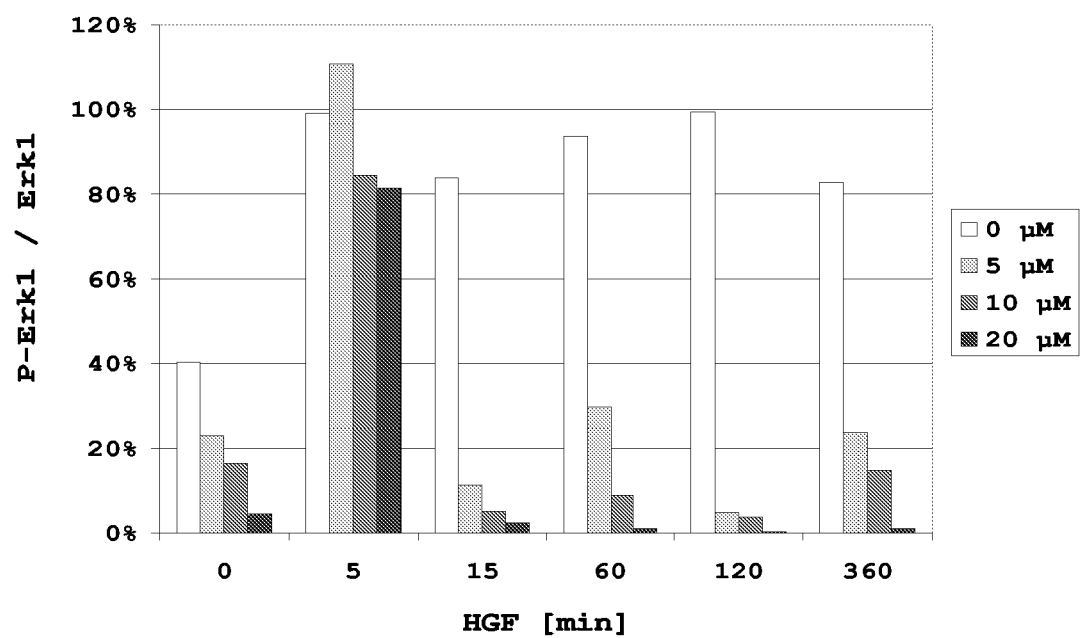

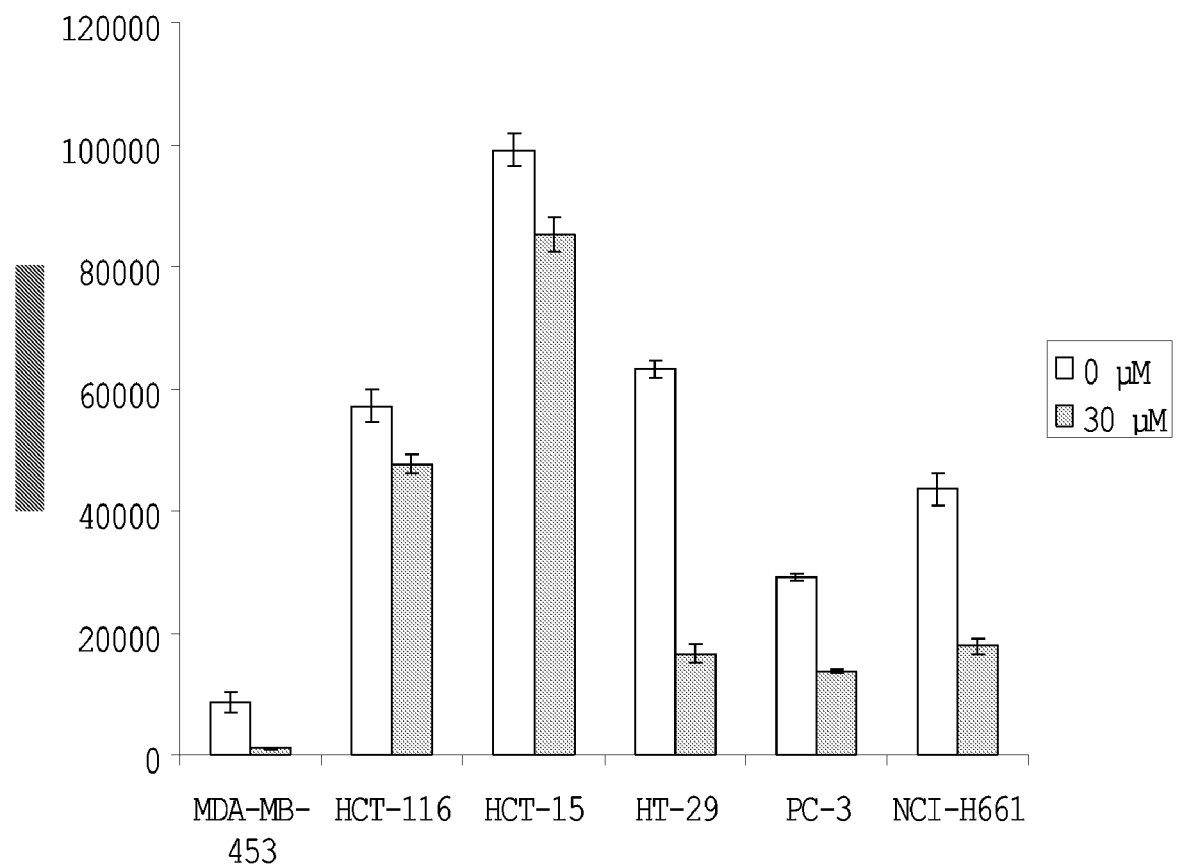
Fig. 5: MTT growth inhibition assay with compound II-1

Fig. 6: Soft agar colony formation assay with compound II-1
A
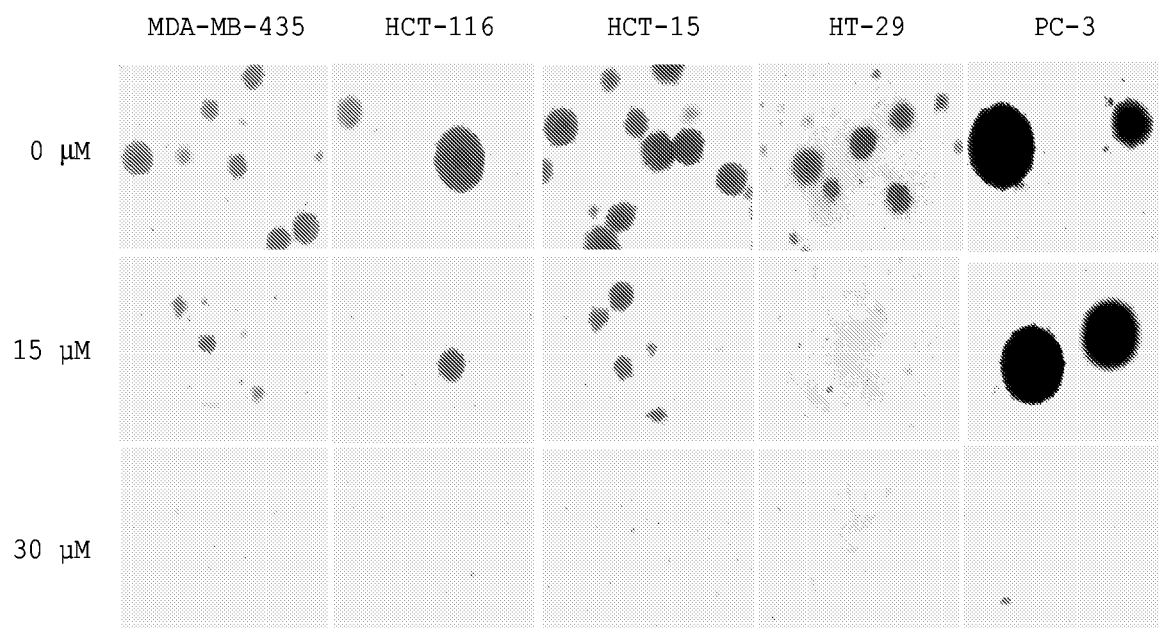
B
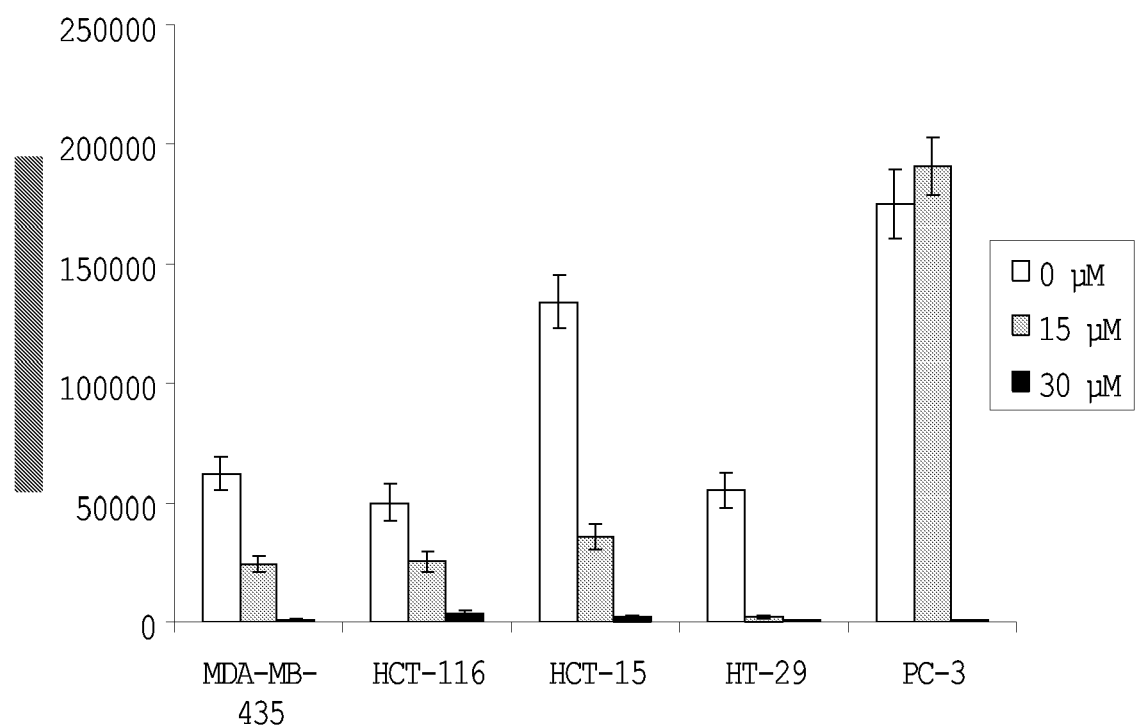

Fig. 7: HGF/SF phosphorylation pssay with NCI-H661 treated with Compound II-1
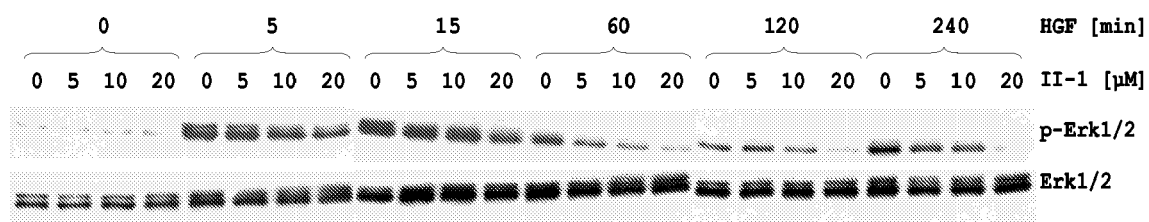

SHP-2 INHIBITORS AND PHARMACEUTICAL COMPOSITIONS COMPRISING THEM

The present invention relates to small molecule protein tyrosine phosphatase inhibitors, especially Shp-2 inhibitors, of formulae (I) and/or (II), and to pharmaceutical compositions comprising them. The invention is also directed to the use of said compounds for the treatment of phosphatase-mediated diseases, especially cancer and metastasis. The invention further concerns a method for treating a proliferative disease, a genetic disorder, an autoimmune disease, an angiogenic disorder or cancer in a patient in need of such treatment, comprising administering to said patient a therapeutically effective amount of at least one compound of formula (I) and/or (II).

Metastases are defined as distant settlements of primary tumor cells. Sooner or later during the development of most types of human cancer, primary tumor masses generate pioneer cells that move out, invade adjacent tissues, and travel to distant sites where they may succeed in founding new colonies. The capability for invasion and metastasis enables cancer cells to escape the primary tumor mass and colonize new terrain in the body where, at least initially, nutrients and space are not limiting. Metastases are one of the greatest sources of pain in late stage cancer.

Hepatocyte growth factor/scatter factor (HGF/SF), its receptor, the tyrosine kinase Met, and the downstream signaling adapter Gab1 are important mediators of invasive growth which comprises increased proliferation, cell-cell dissociation and motility, matrix degeneration and survival of epithelial cells. HGF/SF is a strong inducer of angiogenesis in vivo, a process that is also important for blood vessel formation in tumors. All these processes become important during metastasis (Birchmeier et al., 2003).

Under physiological conditions, the formation and patterning of an embryo, wound healing, axon guidance or organ regeneration is adjusted by the HGF/Met/Gab1 system. The importance of these proteins in development is shown by the embryonic lethality of HGF/SF, Met or Gab1 null-mutations. Nearly identical phenotypes verify these factors as key components of Met signal transduction.

The Met receptor was originally identified in a constitutively active mutant form (Tpr-Met) as an oncogene. A variety of human solid tumors (i.e. breast, thyroid, prostate, hepatocellular, colorectal and gastric carcinoma) demonstrate aberrant Met activity due to HGF-dependent autocrine loop, Met overexpression, gene amplification or gene mutations. Experimentally, expression of HGF and Met or mutant Met conferred malignant properties on normal cells (motility, invasion, tumorigenicity) (Jeffers et al., 1998). Clinically, HGF/Met overexpression has been shown to correlate with poor prognosis in several types of cancer. Therefore, the Met signaling system has been regarded as a promising therapeutic target in the treatment of cancer and especially metastasis.

Polypeptide growth factors and cytokines usually elicit their effects by activating specific cell-surface receptors, thereby initiating signaling cascades. The binding of such a ligand termed HGF/SF to its receptor Met initiates the dimerization and phosphorylation of Met. Upon activation by HGF/SF, Met accumulates a variety of adapter and signal proteins like Gab1, Grb2, CRKL, PI(3)K and Shp-2, forming the Met-signaling complex. The docking protein Gab1 binds the phosphorylated Met receptor tyrosine kinase directly and mediates signals of Met in cell culture. Gab1 is phosphorylated by Met and by other receptor and nonreceptor tyrosine kinases. Gab1-SHP2 interaction activates SHP2 by binding to tyrosine-based activation motifs or by deletion of the N-SH2 domain.

Shp-2 is a 68 kD protein tyrosine phosphatase with two Src homology 2 (SH2) domains (N-SH2 and C-SH2) located in the N-terminal region and two potential Grb2 SH2 domain binding sites located in the C-terminal region. It is also known as SHPTP2, Syp, PTP1D and PTP2C. Shp-2 is basely inactive due to auto-inhibition by its N-SH2 domain. The enzyme is activated by interaction with a variety of components and acts as a positive regulator of cell proliferation.

The primary function of Gab1 association with an activated Shp-2 in MAP kinase activation includes targeting of the activated Shp-2 to the membrane.

It could be shown that the tyrosine phosphatase Shp-2 is an important downstream signaling molecule of Met/Gab1 for the activation of the mitogen activated protein (MAP) kinase pathway which can lead to cell transformation, a prerequisite for the development of cancer.

Association of Gab1 with Shp-2 (but not with PI3K, CRKL or Grb2) was essential to induce a branching morphogenesis program (Schaeper et al., 2000). The phenotypes observed in this assay allow monitoring of dissociation, motility and invasiveness of epithelial cells in vitro, therefore the results of this assay can be correlated with the metastatic potential of transformed cells in vivo.

Besides branching morphogenesis, the scattering assay is an alternative in vitro model system to evaluate the potential metastatic capacity of epithelial cells. Also here, Shp-2 plays a prominent role since interference with Shp-2 function (by a dominant-negative Shp-2 mutant) inhibits HGF/SF induced cell scattering of epithelial cells (Kodama et al., 2000). This phenotype is reminiscent of direct interference with Met activity itself. The development of specific Shp-2 inhibitors should therefore allow blocking or reducing aberrant Met activity and provide an excellent means for the treatment of HGF/Met-dependent metastases.

Similar to the Met activation by HGF/SF, the epidermal growth factor (EGF) dependent transactivation at the EGF receptor can be blocked by either interfering with Shp-2 binding to Gab1 or with a catalytically inactive Shp-2 mutant (Bennett et al., 1996) demonstrating the important role of Shp-2 in growth factor-induced mitogenesis. Shp-2 activates a signaling step downstream of Gab1 and upstream of Src and Ras in the MAP kinase pathway.

Shp-2 was shown to negatively regulate the association of Gab1 with RasGAP by dephosphorylation of a RasGAP binding site on Gab1 (Gab1-Y317), which leads to a sustained MAP kinase signaling via Ras.

It is known that specific Met signaling antagonists may have important therapeutic potential for the treatment of cancers in which Met signaling contributes to an invasive/metastatic phenotype. A peptide representing the carboxy-terminal tail of Met inhibits its kinase activity and invasive growth of epithelial cells. Dominant-negative Met stably expressed in a tumor cell line delays tumor growth and metastases in a mouse model. Another Met antagonist protein NK4 inhibits tumor growth and metastases in an orthotopic mouse model with intraperitoneal administration and in a xenograft mouse model with adenoviral transfer of the therapeutic gene. Disadvantages that must be addressed when preparing proteins/peptides for delivery include the large size, hydrophilicity, and physical and chemical lability of these molecules. Viral delivery of proteins/peptides encoding genes is also problematic because of high immunogenity of the viral coat proteins which can result in an immune response in the patient.

Also chemical compounds have been described as Met signaling antagonists: geldanamycin derivatives, originally described as anisamycin antibiotics, inhibit HGF/SF-mediated plasmin activation and cell motility/invasion and downregulate Met protein expression (Webb et al., 2000), but they act indirectly via interference with Hsp90 chaperone function.

The staurosporine derivative K252a, originally described as a serine/threonine kinase inhibitor, inhibits Met autophosphorylation and HGF induced scattering in vitro and the ability of Met dependent tumorigenic cell lines to form lung metastases in a nude mouse model (Morotti et al., 2002). The malignant cells in these experiments had to be pretreated with the compound in vitro before they were injected into the caudal vein of the animals. K252a had turned out to show no antitumor activity in vivo in earlier experiments.

However, prior art compounds derived from natural products often possess high molecular weights and several stereo centers which require challenging synthetic efforts for their improvement and use as anti-cancer drugs. Furthermore, the early impact into the signaling cascade may affect branched pathways downstream of Met or Gab1 probably causing severe side effects.

Because the Shp-2 phosphatase is a positive mediator of growth factor signaling, especially in the Ras pathway, its inhibition should be of therapeutic benefit. For example, patients who suffer from Noonan Syndrome in combination with juvenile myelomonocytic leukemia (JMML) carry germline mutations in their SHP-2/PTPN11 gene. Somatic mutations in PTPN11 account for 34% of non-syndromic JMML (without Noonan Syndrome). Furthermore, mutations in PTPN11 were found in a small percentage of individuals with Myelodysplastic Syndrome (MDS) and de novo Acute Myeloid Leukemia (AML). Interestingly, these mutations result in an increased phosphatase activity of Shp-2. This gain-of-function phenotype leads to increased activation of the Ras/MAP kinase pathway and increased cell proliferation, a prerequisite for generation of leukemia. JMML accounts for 30% of all childhood cases of MDS and 2% of all leucemic diseases. Inhibition of phosphatase activity of Shp-2 should be of therapeutic benefit for such patients and the development of specific Shp-2 inhibitors should therefore be an excellent means, also for the treatment of EGF/EGFR dependent tumors of epithelial origin which represent the vast majority of cancers (e.g. breast and prostate carcinomas).

It is known that Shp-2 can be modulated by antisense nucleic acids. Such molecules are described in U.S. Pat. No. 6,200,807 B1 (Isis Pharmaceuticals Inc.). Herein, SHP2 antisense nucleic acids are delivered to cells by a transfection agent, and the influence of this delivery on SHP2 mRNA expression levels is measured by Northern blotting or real-time PCR, on Shp-2 protein levels by Western blotting. A subset of the analyzed antisense molecules is able to decrease SHP2 mRNA levels in cell culture more than 40-50%. Antisense nucleic acids are highly charged large molecules which have to be delivered to cells usually by transfection reagents (e.g. liposomal formulations) or genetically encoded (e.g. by plasmids or viral vectors).

An alternative method to interfere with gene function is RNA interference (RNAi). Silencing ribonucleic acids (siRNAs), 20-22 nucleotides in length, are delivered to cells which results in a degradation of the corresponding mRNAs by a cellular machinery. Such oligonucleotides are described in U.S. 2004/0077574 A1 (Ceptyr Inc.). Herein, different Shp-2 specific siRNAs result in 10-50% inhibition of cell proliferation of various cell types. As for antisense nucleic acids, siRNAs are highly charged large molecules which have to be delivered to cells usually by transfection reagents (e.g. liposomal formulations) or genetically encoded (e.g. by plasmids or viral vectors).

But these technologies are neither established nor are the nucleic acids and derivatives thereof well suited for simple administration.

Well-known small molecules which are described in the prior art as inhibitors of phosphatases contain either one or two carboxylate groups or difluoromethylenphosphonate groups to mimic the two formal charges present on phosphate at physiological pH. Most advanced are such inhibitors for modulating enzyme activity of PTP1B, a common drug target in diabetes type II (insulin resistance). The development of such inhibitors is an active area of research and has been extensively reviewed (Huijsduijnen et al., 2004). Most of the described potent phosphotyrosine mimetics contain at least two acids and lead to inhibitors with poor cellular permeability.

Sulfhydantoins have been described as uncharged small molecule inhibitors of Shp-2 in WO 2004/062664 A1 (Vertex Pharmaceuticals Inc.). The three best compounds described there inhibit pNPP hydrolysis with IC50 values ranging from 1 to 100 µM. No cellular activity of these Shp-2 inhibitors is described.

At present, there are no effective compounds available for modulating Met signaling system and/or for treatment of HGF/Met-dependent diseases.

Therefore, the technical problem underlying the present invention is to provide compounds which allow blocking or reducing aberrant Met activity.

This problem is solved by the provision of the embodiments as defined in the claims of the present invention. It has been found that the compounds of formula (I) or (II) or their mixtures effectively inhibit a protein tyrosine phosphatase, especially Shp-2, which makes them suitable for treating HGF/met-dependent diseases which can be affected positively by inhibiting Shp-2.

Briefly, the present invention provides pharmaceutical compositions comprising as active substance at least one compound of general formulae (I) or (II):

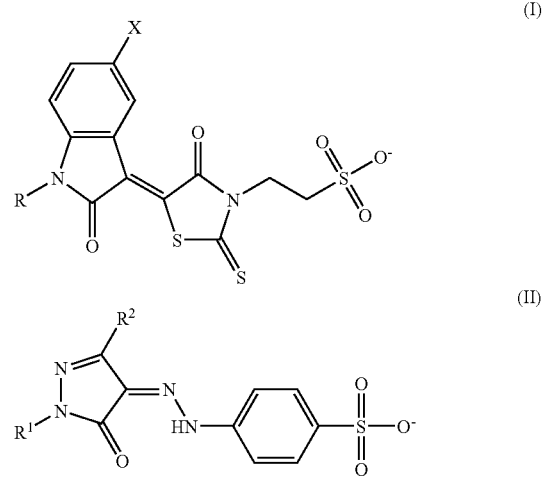

or a mixture of substances of formula (I) and (II) or pharmaceutically acceptable salts or solvates thereof, wherein R is an unsubstituted or substituted group selected from aryl, heteroaryl, arylalkyl, heteroarylalkyl, (arylcarbamoyl)alkyl or (heteroarylcarbamoyl)alkyl X is hydrogen, a halogen atom, a hydroxy, carboxy, alkyl, haloalkyl, alkoxy or nitro group and $R^1$ and $R^2$ are, independently from each other, an unsubstituted or substituted group selected from aryl or heteroaryl.

The pharmaceutical compositions of the invention comprise the compounds of formula (I) and/or (II) preferably as sulfonic acids, their salts or esters.

The sulfonic acid of formula (I) with X=bromine and R=benzyl is excluded from the pharmaceutical composition according to the invention.

It has been surprisingly found that these compounds are useful as specific Shp-2 inhibitors. Advantageously, they are small molecules that possess optimal pharmako-kinetic properties such as for instance water solubility and membrane permeability.

The compounds of formula (I) and (II) and the pharmaceutical compositions thereof, are useful for treating or reducing the risk of a variety of disorders, such as for instance cancers and autoimmune diseases. In particular, administration of such a compound to a patient could be a benefit if the disease is caused by aberrant enzyme activity of a phosphatase such as Shp-2, e.g. by an activating mutation in the SHP2/PTPN11 gene which is the case e.g. in Noonan syndrome and juvenile myelomonocytic leukemia.

The present invention is based on the finding of sulfonate/sulfonic acid group containing molecules as phosphotyrosine mimetics. The present invention describes the novel use of compounds containing an 2-(5-(2-oxoindolin-3-yliden)-4-oxo-2-thioxothiazolidin-3-yl)-ethansulfonate (I) or an 4-(2-(5-oxo-1,5-dihydro-4H-pyrazol-4-ylidene)hydrazino)-benzenesulfonate (II) group as phosphatase enzyme modulators. In particular, it has been found that the compounds of formula (I) and (II) and the pharmaceutical compositions thereof, are effective as inhibitors of the Shp-2 phosphatase.

In a preferred embodiment of the invention R in formula (I) represents (arylcarbamoyl)alkyl, preferably (phenylcarbamoyl)alkyl, most preferred (phenylcarba-moyl)methyl. The (arylcarbamoyl)alykl group can be unsubstituted or substituted. In a preferred embodiment it is substituted in 3- or 4-position of the phenyl moiety with $C_1$-$C_4$-alkoxy, preferably methoxy or ethoxy, halogen, trifluoroalkyl or trichloroalkyl, preferably trifluoromethyl.

In a further embodiment of the invention R in formula (I) is unsubstituted or substituted aryl, preferably benzyl or in 4-position with $C_1$-$C_4$-alkyl substituted benzyl.

In an especially preferred embodiment R in formula (I) is 4-ethoxyphenylcarbamoyl)methyl, (3-bromophenylcarbamoyl)-methyl, (4-fluorophenylcarbamoyl)methyl, (3-(trifluoromethyl)phenylcarbamoyl)methyl, 4-methylbenzyl or benzyl.

Regarding substituent X in formula (I) alkoxy means preferably $C_1$-$C_4$-alkoxy, especially methoxy and ethoxy, and alkyl means preferably $C_1$-$C_4$-alkyl, especially methyl. Haloalkyl preferably represents a perhalogenated group $C_nHal_{2n+1}$ with n being 1 or 2 and Hal being fluorine or chlorine, particularly trifluoromethyl or trichloromethyl. In a preferred embodiment X is hydrogen or a bromine atom.

According to a particularly preferred embodiment of the invention the active substance of formula (I) is 2-(5-(1-((4-ethoxyphenylcarbamoyl)methyl)- 2-oxoindolin-3-yliden)-4-oxo-2-thioxothiazolidin-3-yl)-ethansulfonic acid or -ethansulfonate (I-1)

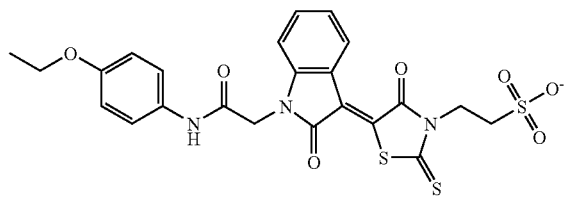

(I-1)

(Chemical Diversity Labs, San Diego, Substance CDL 4340-0580)

In an other embodiment of the invention $R^1$ in formula (II) represents phenyl or heteroaryl selected from the group consisting of thiazolyl, pyridinyl, pyrimidinyl, imidazolyl, or triazolyl, preferably 1,2,4-triazolyl. The phenyl or heteroaryl moieties may also be substituted. In a preferred embodiment $R^1$ represents aryl or heteroary substituted with alkyl, alkylamino, halogen, haloalkyl, carboxy, alkoxycarbonyl, hydroxy, N-morpholino, N-morpholinoalkyl, N-morpholinocarbonyl, N-methyl-N-piperazinyl, N-methyl-N-piperazinylalkyl, N-methyl-N-piperazinylcarbonyl or sulfonic acid group, preferably phenyl substituted in 4-position.

In an especially preferred embodiment R1 is 4-fluorophenyl, 4-trifluorophenyl, 4-carboxyphenyl or 4-ethoxycarbonylphenyl. Thiazolyl means in a preferred embodiment thiazol-2-yl and substituted thiazolyl means preferably embodiment thiazol-2-yl substituted with phenyl, preferably in 4-position.

$R^2$ in formula (II) preferably represents phenyl or phenyl substituted with nitro, halogen, preferably chlorine or fluorine, haloalkyl, preferably trifluoroalkyl or trichloroalkyl, carboxy, alkoxycarbonyl, hydroxy or a sulfonic acid group, preferably in 4-position. In an especially preferred embodiment of the invention $R^2$ is 4-nitrophenyl-, 4-chlorophenyl, 4-fluorophenyl, 4-trifluoromethylphenyl, 4-carboxyphenyl, 4-ethoxycarbonylphenyl, 4-hydroxyphenyl or 4-sulfophenyl.

According to a particularly preferred embodiment of the invention the active substance of formula (II) is 4-(2-(3-(4-nitrophenyl)-5-oxo-1-phenyl-1,5-dihydro-4H-pyrazol-4-ylidene)hydrazino)-benzenesulfonic acid or -benzenesulfonate (II-1)

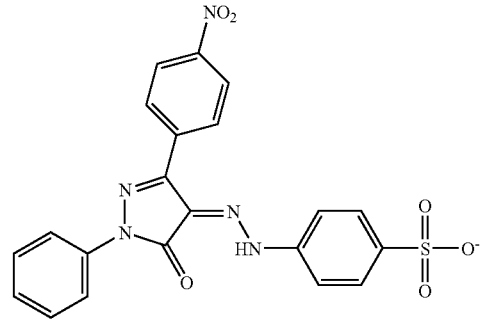

(II-1)

(Vitasmlab, Moskau, Substance TRG 020 339)

Unless otherwise defined, all technical and scientific terms used herein have the same meaning as commonly understood by a person of ordinary skill in the art to which this invention belongs. Although methods and materials similar or equivalent to those described herein can be used in the practice or testing of the present invention, suitable methods and materials are described below. All publications, patent applications, patents, and other references discussed above are provided solely for their disclosure prior to the filing date of the present application. Nothing herein is to be construed as an admission that the invention is not entitled to antedate such disclosure by virtue of its prior invention. All publications, patent applications, patents, and other references mentioned herein are incorporated by reference in their entirety including all figures and drawings.

The phrase "substituted group" means that it may have a substituent at each substitutable position, and each substitution is independent of any other substitutions. Exemplary substituents may include but are not limited to one or more of the following groups: halogen (such as F, Cl, Br, I), hydroxy, carboxy (—CO—OH), alkyl, cycloalkyl, haloalkyl (such as trichloromethyl and trifluoromethyl), alkoxy, alkylthio, alkyloxycarbonyl (R—O—CO—), alkylcarbonyloxy (R—CO—O—), nitro, cyano, amino (—$NH_2$), alkylamino, dialkylamino, carbamoyl (—NH—CO—OR— or —OC—O—NHR—), alkylsulfonyl, alkylsulfinyl, alkylthio, thiol (—SH), urea (—NH—CO—NHR) or sulfonamide. Alkyl groups as defined may also comprise one or more carbon to carbon double bonds or one or more carbon to carbon triple bonds.

The term "alkyl" refers to a monovalent alkane (hydrocarbon) derived radical containing from 1 to 20 carbon atoms unless otherwise defined. An alkyl group is an optionally substituted straight or branched hydrocarbon group. When substituted, alkyl groups may substituted with a residue R at any available point of attachment. Examples of unsubstituted alkyl groups may include but are not limited to methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "aryl" refers to monocyclic, bicyclic, tricyclic or tetracyclic aromatic rings, e.g. phenyl ($C_6H_5$—) and the like, as well as groups which are fused, e.g. naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. According to the present invention the term "aryl" also covers the benzyl group.

The term "heteroaryl" refers to a monocyclic aromatic hydrocarbon group having 5 or 6 ring atoms, a bicyclic aromatic group having 8 to 10 atoms, or a tricyclic aromatic group having 11 to 14 atoms containing at least one heteroatom (O, S, or N) in which a carbon or nitrogen atom is the point of attachment, and in which one to three additional carbon atoms is optionally replaced by a heteroatom selected from O, N, or S, said heteroaryl group being optionally substituted as described herein. Exemplary heteroaryl groups may include but are not limited to the following: thienyl, furyl, pyrrolyl, pyridinyl, imidazolyl, oxazolyl, pyrrolidinyl, piperidinyl, thiazolyl, pyrazinyl, pyridazinyl, pyrimidinal, triazinylazepinyl, indolyl, isoindolyl, quinolinyl, isoquinolinyl, benzothiazolyl, benzoxazolyl, benzimidazolyl, benzoxadiazolyl, benzofuranzanyl.

The term "arylalkyl" denotes an aromatic ring as described above bonded to an alkyl group as described above.

The term "alkoxyl" denotes an alkyl group as described above bonded through an oxygen linkage(—O—).

The term "heteroatom" means oxygen (O), sulfur (S) or nitrogen (N), selected on an independent basis.

The term "halogen" refers to chlorine (Cl), bromine (Br), fluorine (F) or iodine (I).

Suitable salts of the sulfonate group, like sodium, potassium, lithium or magnesium or other pharmaceutically acceptable salts are also included. Sulfonates in the protonated form as sulfonic acids (—$SO_2$—OH), and as sulfonic acid esters (—$SO_2$—OR) and optionally substituted sulfonic acid amides(—$SO_2$—$NH_2$, —$SO_2$—$NHR_1$, —$SO_2$—$NR_1R_2$) with $R_1$ and $R_2$ independently being hydrogen or $C_1$-$C_4$ alkyl are also within the scope of the present invention.

All isomers of the compounds of the instant invention are included, either in a mixture or in pure or substantially pure form.

Compounds of this invention may exist in alternative tautomeric forms. Unless otherwise indicated, the representation of either tautomer is meant to include the other.

Solvates (e.g. hydrates) of the compounds of formula (I) and (II) are also within the scope of the present invention. Methods of solvation are generally known in the art. Accordingly, the compounds of the instant invention may be in the free or hydrate form, and may be obtained by methods exemplified.

The present invention is based on the finding of sulfonate and sulfonic acid groups containing molecules that are useful as mimics of molecules that contain tyrosinephosphate groups.

In a preferred embodiment of the invention, the sulfonate/sulfonic acid group containing molecules of formula (I) and/or (II) may be useful as reversible inhibitors of enzymes such as phosphatases. Additionally, they can be used as probes in X-ray or NMR based structure analysis of proteins, preferably for co-crystallization of a the Shp-2 phosphatase domain together with a small molecule inhibitor.

According to the invention the compounds of formulae (I) or (II) inhibit proteins selected from the group comprising phosphatases, Src homology 2 (SH2) and phosphotyrosine binding (PTB) domains containing proteins and phosphotyrosine-binding proteins. Preferably, they inhibit protein tyrosin phosphatases (PTP). More preferably, the protein tyrosin phosphatase is Shp-2 or an oncogenic variant or point mutant of Shp-2.

In another preferred embodiment said compounds are used in cell culture to interfere with phosphatase dependent functions such as cell proliferation, cell-cycle progression, cell-cell dissociation, cell polarity, cell motility, matrix degeneration, invasion and stem cell renewal. Hence, the invention is also directed to the use of compounds of formulae (I) and/or (II) as protein tyrosine phosphatase inhibitor, preferably Shp-2 inhibitor, for the investigation of cellular processes in biological in vitro, in vivo or ex vivo systems, e.g. cell cultures.

The pharmaceutical compositions comprising as active substances the compounds of formula (I) and/or (II) may also comprise conventional auxiliary substances, preferably carriers, adjuvants and/or vehicles. For example, said carriers can be fillers, extenders, binders, humectants, disintegrants, dissolution retarders, absorption enhancers, wetting agents, adsorbents, and/or lubricants.

The pharmaceutical composition of the invention may be prepared as a gel, powder, tablet, sustained-release tablet, premix, emulsion, infusion formulation, drops, concentrate, granulate, syrup, pellet, bolus, capsule, aerosol, spray and/or inhalant and/or used in this form. The tablets, coated tablets, capsules, pills and granulates can be provided with conventional coatings and envelopes optionally including opacification agents, and can be composed such that release of the active substance(s) of formulae (I) and (II) takes place only or preferably in a particular part of the intestinal tract, optionally in a delayed fashion, to which end polymer substances and waxes can be used as embedding materials.

For example, the pharmaceutical composition of the present invention can be administered orally in any orally tolerable dosage form, including capsules, tablets and aqueous suspensions and solutions, without being restricted thereto. In case of tablets for oral application, carriers frequently used include microcrystalline cellulose, lactose and corn starch. Typically, lubricants such as magnesium stearate can be added. For oral administration in the form of capsules, useful diluents such as lactose and dried corn starch are employed. In oral administration of aqueous suspensions the active substance is combined with emulsifiers and suspending agents. Also, particular sweeteners and/or flavors and/or coloring agents can be added, if desired.

The active substance(s) can also be present in micro-encapsulated form, optionally with one or more of the above-specified carriers.

In addition to the active substance(s), suppositories may include conventional water-soluble or water-insoluble carriers such as polyethylene glycols, fats, e.g. cocoa fat and higher esters (for example, $C_{14}$ alcohols with $C_{16}$ fatty acids) or mixtures of these substances.

In addition to the active substance(s), ointments, pastes, creams and gels may include conventional carriers such as animal and vegetable fats, waxes, paraffins, starch, tragacanth, cellulose derivatives, polyethylene glycols, silicones, bentonites, silicic acid, talc and zinc oxide or mixtures of these substances.

In addition to the active substance(s), powders and sprays may include conventional carriers such as lactose, talc, silicic acid, aluminum hydroxide, calcium silicate and polyamide powder or mixtures of these substances. In addition, sprays may include conventional propellants such as chlorofluorohydrocarbons.

In addition to the active substance(s), i.e., the composition according to the invention, solutions and emulsions may include conventional carriers such as solvents, solubilizers, and emulsifiers such as water, ethyl alcohol, isopropyl alcohol, ethyl carbonate, ethyl acetate, benzyl alcohol, benzyl benzoate, propylene glycol, 1,3-butylene glycol, dimethylformamide, oils, especially cotton seed oil, peanut oil, corn oil, olive oil, castor oil and sesame oil, glycerol, glycerol formal, tetrahydrofurfuryl alcohol, polyethylene glycols, and fatty esters of sorbitan, or mixtures of these substances. For parenteral application, the solutions and emulsions may also be present in a sterile and blood-isotonic form.

In addition to the active substance(s), suspensions may include conventional carriers such as liquid diluents, e.g. water, ethyl alcohol, propylene glycol, suspending agents, e.g. ethoxylated isostearyl alcohols, polyoxyethylene-sorbitol and sorbitan esters, microcrystalline cellulose, aluminum metahydroxide, bentonite, agar, and tragacanth, or mixtures of these substances.

The pharmaceutical compositions can be present in the form of a lyophilized sterile injectable formulation, e.g. as a sterile injectable aqueous solution or aqueous or oily suspension. Such a suspension can also be formulated by means of methods known in the art, using suitable dispersing or wetting agents (such as Tween 80) and suspending agents.

Preferably, the active substance according to the invention should be present in the above-mentioned pharmaceutical formulations at a concentration of about 0.01 to 99.9, more preferably about 0.05 to 99 wt.-% of the overall mixture.

In addition, the above-mentioned pharmaceutical formulations may include one or more active substances of formulae (I) and/or (II) and optionally further pharmaceutical active substances, but also, in addition to said further pharmaceutical active substances, salts, buffers, vitamins, sugar derivatives, especially saccharides, enzymes, vegetable extracts and others. Buffers and sugar derivatives advantageously reduce the pain during subcutaneous application, and enzymes such as hyaluronidase increase the effectiveness. The production of the pharmaceutical formulations specified above proceeds in a usual manner according to well-known methods, e.g. by mixing the active substance(s) with the carrier(s).

According to the invention the active substances of formula (I) or (II) or mixture of substances of formula (I) and (II) are incorporated in a pharmaceutical formulation at a concentration of 0.1 to 99.5, preferably 0.5 to 95, and more preferably 20 to 80 wt.-%. That is, the active substance is present in the above pharmaceutical formulations, e.g. tablets, pills, granulates and others, at a concentration of preferably 0.1 to 99.5 wt.-% of the overall mixture. Those skilled in the art will be aware of the fact that the amount of active substance will vary depending on the patient to be treated and on the particular type of administration. Once the condition of the patient has improved, the proportion of active substance in the formulation can be modified so as to obtain a maintenance dose that will bring the disease to a halt.

In addition to oral ingestion, intramuscular or subcutaneous injections, or injections into the blood vessels can be envisaged as another preferred route of therapeutic administration of the composition according to the invention. At the same time, influx via catheters or surgical tubes can also be used, e.g. via catheters directly leading to particular organs such as kidneys, liver, spleen, intestine, lungs, etc.

In a preferred embodiment, the pharmaceutical composition of the invention can be employed in a total amount of preferably 0.05 to 500 mg/kg body weight per 24 hours, more preferably 5 to 100 mg/kg body weight. Advantageously, this is a therapeutical quantity which is used to prevent or improve the symptoms of a disorder or responsive, pathological physiological condition.

Obviously, the dose will depend on the age, health and weight of the recipient, degree of the disease, type of required simultaneous treatment, frequency of the treatment and type of the desired effects, and side-effects. The daily dose of 0.05 to 500 mg/kg body weight can be applied as a single dose or multiple doses in order to furnish the desired results. A person of specialized knowledge in the art can determine the optimum dosages required in each case and the type of application of the active substances.

In another particularly preferred embodiment of the invention the pharmaceutical composition is used in a single administration of from 1 to 100, especially from 2 to 50 mg/kg body weight. In the same way as the total amount per day (see above), the amount of a single dose per application can be varied by a person of specialized knowledge in the art. Similarly, the substances used according to the invention can be employed in veterinary medicine with the above-mentioned single concentrations and formulations together with the feed or feed formulations or drinking water.

A further object of the present invention is the use of at least one compound of formulae (I) or (II) or a mixture of substances of formula (I) and (II) (for manufacturing a pharmaceutical composition) for the treatment of a Shp-2 mediated disease, preferably proliferative diseases, genetic disorders, autoimmune diseases, angiogenic disorders and cancer.

According to a preferred embodiment, the invention provides a method for treating or lessening the severity of a Shp-2-mediated disease or condition in a patient comprising administering to said patient an effective amount of at least one compound of formula (I) or (II) or a mixture of substances of formula (I) and (II) of the invention. The term "Shp-2-mediated disease", as used herein means any disease or other deleterious condition in which Shp-2 is known to play a role. Such conditions include, without limitation, genetic disorders, autoimmune diseases, proliferative diseases, angiogenic disorders, and cancers.

Genetic disorders which may be treated or prevented by the compounds of formula (I) or (II) include, but are not limited to Noonan syndrome.

A proliferative disease which may be treated or prevented by the compounds of formula (I) or (II) is a neoplasia, which includes, but is not limited to leukemias, lymphomas, sarcomas, carcinomas, neural cell tumors, undifferentiated tumors, sensinomas, melanomas, neuroblastomas, multiple myeloma, mixed cell tumors, metastatic neoplasia and neoplasia due to pathogenic infections. Leukemias include acute myelogenous leukemia, chronic myelogenous leukemia and juvenile myelomonocytic leukemia.

Angiogenic disorders which may be treated or prevented by the compounds of formula (I) or (II) include, but are not limited to ocular neovasculization and infantile haemangiomas.

Therefore, the invention relates to the use of the compounds of formula (I) and/or (II) in the treatment of metastasis, angiogenesis or autoimmunodeficiency and in the treatment of diseases associated with. These can be inflammatory reactions, autoimmune diseases, e.g. diabetes, obesity, and diseases associated with cell division disorders, such as cancer. The substances of formula (I) or (II) are suitable in the therapy of solid tumors such as for instance breast, thyroid, prostate, hepatocellular, colorectal and gastric carcinoma and their metastases.

Therefore the invention also relates to a method for treating a cancer in a patient or animal in need of such treatment comprising administering to said patient or animal a safe and effective amount of at least one compound of formula (I) or (II) or a mixture of substances of formula (I) and (II).

Beside the treatment of gastric carcinoma the compounds of formula (I) or (II) are also suitable for treating *helicobacter pylori* infections and gastric ulcers which may be caused by such infections. It is assumed that about 35% of the German population is infected with *helicobacter pylori* bacteria.

For a better understanding of the invention, in the following the terms used are explained.

Inflammations in the meaning of the invention are reactions of the organism, mediated by the connective tissue and blood vessels, to an external or internally triggered inflammatory stimulus, with the purpose of eliminating or inactivating the latter and repairing the tissue lesion caused by said stimulus.

Autoimmune diseases in the meaning of the invention are diseases entirely or partially due to the formation of autoantibodies and their damaging effect on the overall organism or organ systems, i.e., due to autoaggression.

The term "angiogenesis" refers to the generation of new blood vessels into cells, tissue, organs or tumors.

The term "metastasis" refers to the process by which tumor cells are spread to distant parts of the body. The term is also used herein to refer to a tumor that develops through the metastatic process.

As used herein, the term "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, to shrink or not metastasize. The specific safe and effective amount or therapeutically effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

"An anti-angiogenic" amount refer to an amount of a compound or composition effective to depress, suppress or inhibit angiogenesis or result in amelioration of symptoms associated with an angiogenic disease. The desired result can be either a subjective relief of a symptom(s) or an objectively identifiable improvement in the recipient of the dosage, a decrease in the vascularization of endothelial cells or a decrease in the rate of angiogenesis as noted by a clinician or other qualified observer.

The terms "treating cancer," "therapy," and the like refer generally to any improvement in the mammal having the cancer wherein the improvement can be ascribed to treatment with the compounds of the present invention. The improvement can be either subjective or objective. For example, if the mammal is human, the patient may note improved vigor or vitality or decreased pain as subjective symptoms of improvement or response to therapy. Alternatively, the clinician may notice decrease in tumor size or tumor burden based on physical exam, laboratory parameters, tumor markers or radiographic findings. Some laboratory signs that the clinician may observe for response to therapy include normalization of tests such as white blood cell count, red blood cell count, platelet count, erythrocyte sedimentation rate, and various enzyme levels. Additionally, the clinician may observe a decrease in a detectable tumor marker. Alternatively, other tests can be used to evaluate objective improvement such as sonograms, nuclear magnetic resonance testing and positron emissions testing.

"Inhibiting the growth of tumor cells" can be evaluated by any accepted method of measuring whether growth of the tumor cells has been slowed or diminished. This includes direct observation and indirect evaluation such as subjective symptoms or objective signs as discussed above.

A further object of the present invention are the compounds of formula (II)

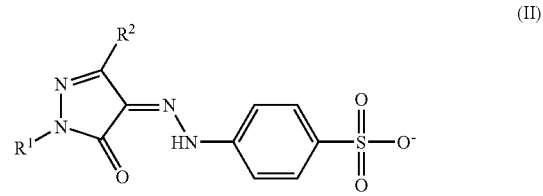

(II)

or pharmaceutically acceptable salts or solvates thereof, wherein $R^1$ is unsubstituted aryl or heteroaryl or aryl or heteroaryl substituted with alkyl, alkylamino, halogen, haloalkyl, carboxy, alkoxycarbonyl, hydroxy, N-morpholino, N-morpholinoalkyl, N-morpholinocarbonyl, N-methyl-N-piperazinyl, N-methyl-N-piperazinylalkyl, N-methyl-N-piperazinylcarbonyl or sulfonic acid group and $R^2$ is phenyl substituted with a nitro, haloalkyl, halogen, carboxy, alkoxycarbonyl, hydroxy or sulfonic acid group with the exclusion of 4-((1,5-dihydro-3-(4-nitrophenyl)-5-oxo-1-phenyl-4H-pyrazol-4-ylidene)-hydrazino)-benzenesulfonic acid (II-1) and 4,4'-(4,5-dihydro-5-oxo-((4-sulfophenyl)-hydrazono)-1H-pyrazole-1,3-diyl)-bisbenzenesulfonic acid. Aryl in $R^1$ is preferably phenyl. Heteroaryl in $R^1$ means preferably thiazolyl, pyridinyl, pyrimidinyl, imidazolyl or triazolyl, preferably 1,2,4-triazolyl.

It is preferred that $R^1$ in formula (II) is phenyl or phenyl substituted with halogen, haloalkyl, carboxy, alkoxycarbonyl, hydroxy, N-morpholino, N-morpholinoalkyl, N-morpholinocarbonyl, N-methyl-N-piperazinyl, N-methyl-N-piperazinylalkyl, N-methyl-N-piperazinylcarbonyl or sulfonic acid group.

The phenyl substituents in $R^1$ or $R^2$ are preferably in 3- or 4-position, especially preferred in 4-position.

In a further embodiment of the invention R¹ in formula (II) is phenyl, 4-halophenyl, preferably 4-fluorophenyl, 4-trifluoromethylphenyl, 4-carboxyphenyl or 4-ethoxycarbonylphenyl.

In an other embodiment of the invention R² in formula (II) is 4-nitrophenyl or 4-halophenyl.

The compounds of formula (I) may be prepared by the following synthetic method:

General Procedure for the Synthesis of Thioxothiazolidines (1-C) (Step 1):

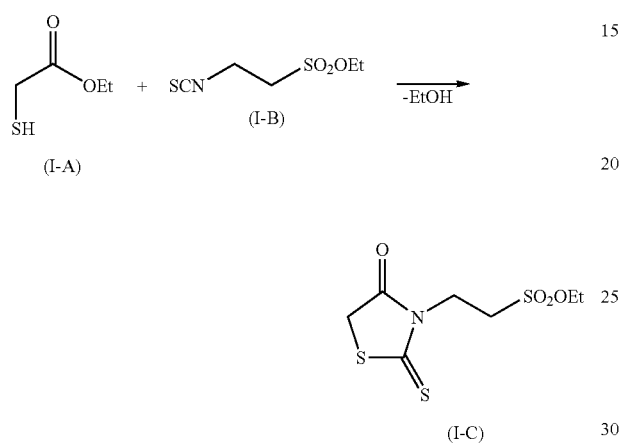

Ethyl 2-mercaptoacetate (I-A) and ethyl 2-isothiocyanato-ethanesulfonate (I-B) or 2-isothiocyanato-ethanesulfonic acid, alternatively, are dissolved in 1,2-dichloroethane and triethylamine is added. The product ethyl 2-(4-oxo-2-thioxothiazolidin-3-yl)-ethanesulfonate (1-C) can be isolated after e.g. 1 h of stirring and subsequent solvent removement.

General Procedure for the Synthesis of N-Alkylated Indoline-2,3-Diones (I-G and I-H) (step 2):

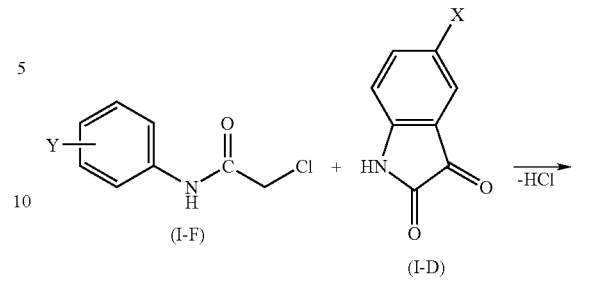

Indoline-2,3-dione (I-D) is either N-alkylated with benzylchloride (I-E) or N-phenyl-2-chloro-acetamid (I-F) to yield the 1-benzylindoline-2,3-dione (I-G) or with the 1-phenylcarbamoylmethylindoline-2,3-dione (I-H), respectively.

General Procedure for the Synthesis of Indolinyliden-Thioxothiazolidines (I-I and I-J) (step 3):

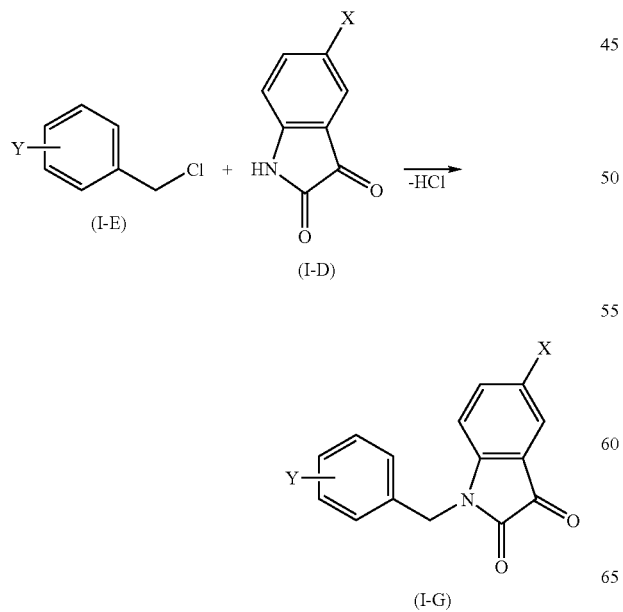

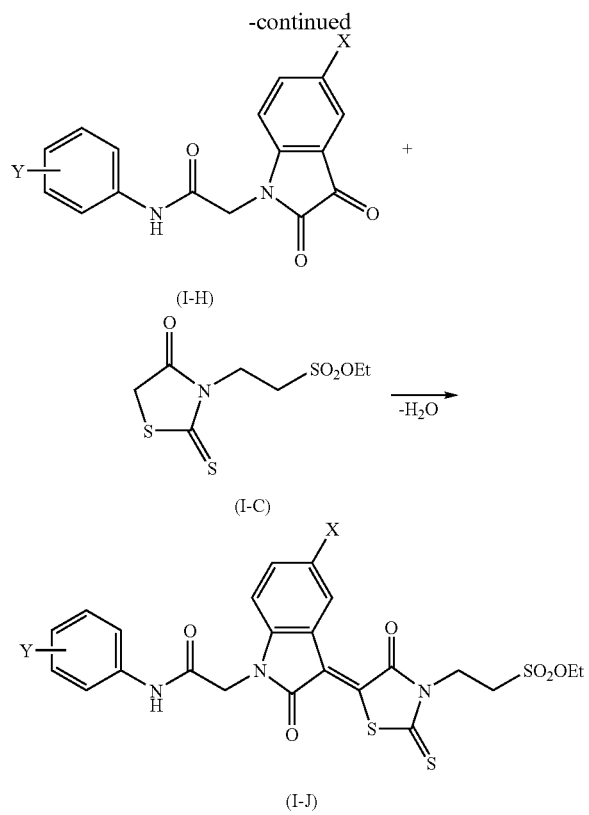

The dioxoindole (I-G) or (I-H) from step 2 is condensed with the thioxothiazolidinone (I-C) from step 1 to yield the sulfonester ethyl 2-(5-(1-benzyl-2-oxoindolin-3-yl iden)-4-oxo-2-thioxothiazolidin-3-yl)-ethansulfonate (I-I) or ethyl 2-(5-(2-oxo-1-phenylcarbamoyl methylindolin-3-yliden)-4-oxo-2 thioxo-thiazolidin-3-yl)-ethansulfonate (I-J), respectively.

General Procedure for the Synthesis of Sulfonates (I-K and I-L) (Step 4):

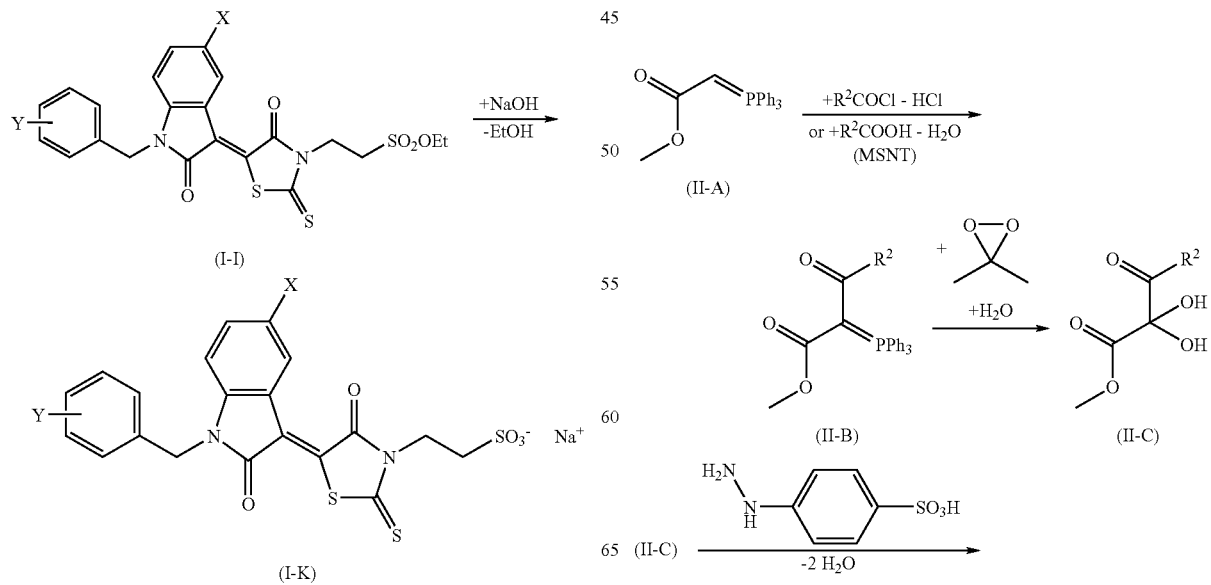

The sulfonester (I-I) or (I-J) from step 3 is hydrolysed with sodium hydroxide to yield the sodium salt of 2-(5-(1-benzyl-2-oxoindolin-3-yliden)-4-oxo-2-thioxothiazolidin-3-yl)-ethansulfonic acid (I-K) or the sodium salt of 2-(5-(2-oxo-1-(phenylcarbamoylmethyl)indolin-3-yl iden)-4-oxo-2-thioxothiazolidin-3-yl)-ethansulfonic acid (I-L), respectively.

Different substitutions of the phenylring of the benzylchloride (I-E) or the N-phenyl-2-chloro-acetamid (I-F) (where Y represents hydrogen or an optionally substituted alkyl or alkoxy group) respectively, and of the condensed phenyl ring of the indoline-2,3-dione (I-D) (where X represents e.g. hydrogen or a F, Cl, Br, OH, $CF_3$, carboxy, sulfo, alkyl, alkoxy or nitro group) result in the corresponding sulfonic acid or its corresponding sodium salt, (I-K) or (I-L), respectively.

The compounds of formula (II) were prepared by the following synthetic methods:

Method 1:

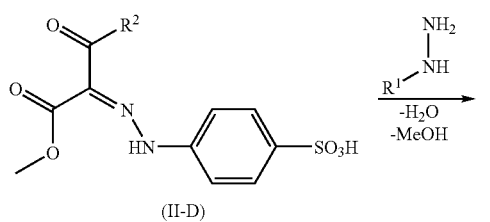

(II-D)

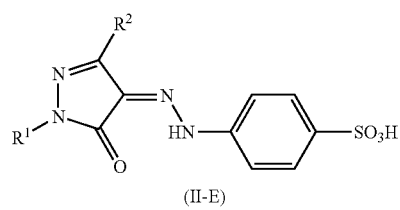

(II-E)

In the first step, methyl 2-(triphenylphosphoranylidene)-acetate (II-A) was acylated with carboxylic acid chloride $R^2COCl$ in the presence of a base like lutidine (alternatively by the carboxylic acid $R^2COOH$ in the presence of the activating reagent 1-(2-mesitylenesulfonyl)-3-nitro-1H-1,2,4-triazol (MSNT)). In the second step, the obtained methyl 3-oxo-2-triphenylphosphoranylidene-propanoate (II-B) was oxidized with dimethyldioxirane (DMDO) to yield the methyl 2,2-dihydroxy-3-oxo-propanoate (II-C). In the third step, this compound was condensed with 4-hydrazinylbenzenesulfonic acid to form the methyl 2-(4-sulfophenylhydrazono)-3-oxo-propanoate (II-D). In the fourth step, this compound was condensed with the hydrazine $R^1NHNH_2$ to form the 4-(2-(1,5-dihydro-5-oxo-4H-pyrazol-4-ylidene)-hydrazino)-benzenesulfonic acid (II-E).

Different substitutions $R^1$ and $R^2$ of the hydrazine $R^1NHNH_2$ and the carboxylic acid chloride $R^2COCl$ (alternatively of the carboxylic acid $R^2COOH$), respectively, resulted in the corresponding benzenesulfonic acids (II-E) where $R^1$ and $R^2$ represent, independently from each other, an unsubstituted or substituted group selected from aryl or heteroaryl.

General Procedure for the Synthesis of Ketophosphoranylides (II-B) (Step 1):

In a nitrogen atmosphere, 1 equivalent of methyl 2-(triphenylphosphoranylidene)-acetate (II-A) was provided in dry dichloromethane (5 ml). A mixture of 1.2 equivalents of carboxylic acid chloride $R^2COCl$ (alternatively, 1.2 equivalents of carboxylic acid $R^2COOH$ in the presence of 1.2 equivalents of MSNT) and 1.1 equivalents of lutidine in dry dichloromethane (5 ml) was added. The reaction mixture was stirred at room temperature in a nitrogen atmosphere for 16 h and subsequently quenched with 5 ml water. The two layers are separated, and the aqueous layer is extracted with dichloromethane two times. The combined organic layers were dried over magnesium sulfate, filtered and concentrated in vacuo. The crude ketophosphoranylide (II-B) was purified by flash chromatography over silica gel employing ethyl acetate/hexane as eluent.

General Procedure for the Synthesis of Hydrated 2,3-Diketoesters (II-C)(Step 2):

3 equivalents of dimethyldioxirane (DMDO; produced by the oxidation of acetone with the oxone triplesalt $KHSO_5.KHSO_4.2K_2SO_4$ in the presence of aqueous sodium hydrogencarbonate at 240 mbar/−78° C.) were added to a solution of ketophosphoranylide (II-B) in dichloromethane. The reaction mixture was stirred at room temperature for 1 h until it was destained, and subsequently concentrated in vacuo. The hydrated 2,3-diketoester (II-C) was purified by flash chromatography over silica gel employing ethyl acetate/hexane as eluent.

General Procedure for the Synthesis of Phenylhydrazones (II-D)(Step 3):

In a nitrogen atmosphere, 1 equivalent of the hydrated 2,3-diketoester (II-C) was dissolved in ethanol (10 ml), and 1.2 equivalents of 4-hydrazinylbenzenesulfonic acid hemihydrate were added. Subsequently, concentrated hydrochloric acid was dropped carefully to the reaction mixture which was boiled afterwards at 85° C. for 16 h under reflux and concentrated in vacuo.

General Procedure for the Synthesis of Pyrazolones (II-E) (Step 4):

In a nitrogen atmosphere, 1 equivalent of the crude phenylhydrazone (II-D) was dissolved in ethanol (10 ml), and 1.2 equivalents of the hydrazine $R^1NHNH_2$ were added. Subsequently, concentrated hydrochloric acid (0.1 ml) was dropped carefully to the reaction mixture which was boiled afterwards at 85° C. for 16 h under reflux. After cooling to room temperature, saturated sodium hydrogenchloride solution was added until the pH of the solution became basic. The solution was subsequently filtrated and partially concentrated in vacuo. The precipitate that was formed after a few hours at 4° C. contained the pure pyrazolone (II-E) which was subsequently isolated by filtration.

Method 2:

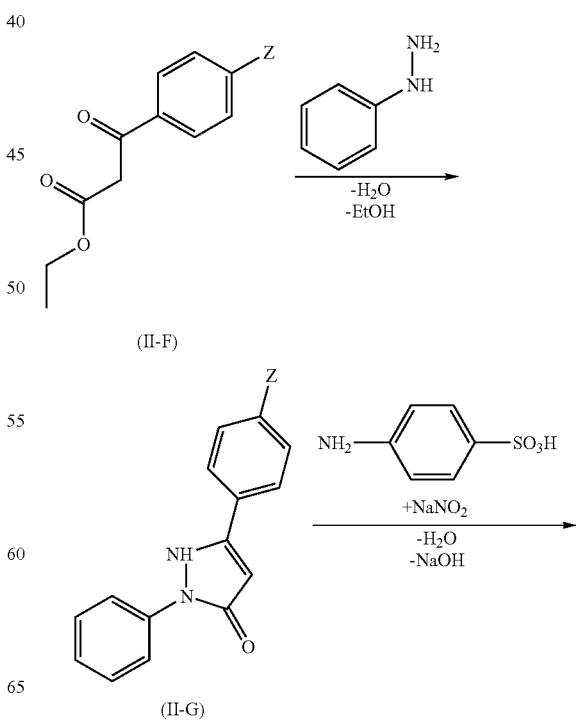

(II-F)

(II-G)

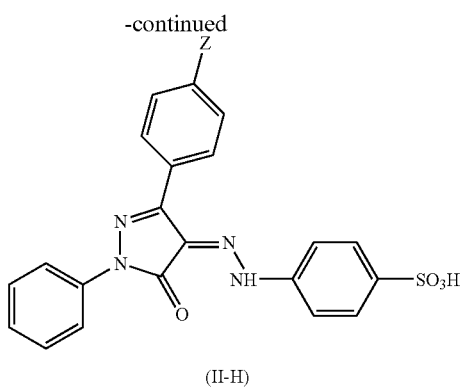

(II-H)

The ketoester ethyl benzoylacetate (II-F) is condensed with phenylhydrazine to yield 1,2-dihydro-1,3-diphenyl-pyrazol-5-one (II-G). Subsequently, 4-aminobenzenesulfonic acid is diazotylated with sodium nitrite in aqueous solution at low pH, and the resulting diazonium salt is immediately converted into 4-(2-(1,5-dihydro-1,3-diphenyl-5-oxo-4H-pyrazol-4-ylidene)-hydrazino)-benzenesulfonic acid (II-H) by adding (II-G). Different substitutions of the phenylring of ketoester (II-G) result in the corresponding sulfonic acids (II-H) where Z represents e.g. hydrogen or a F, Cl, Br, OH, trihaloalkyl, carboxy, alkoxycarbonyl, sulfo or nitro group.

Without intending to be limiting, the invention will be explained in more detail with reference to the following examples.

EXAMPLES

Example 1

Enzymatic pNPP Assay

The catalytic domain of Shp-2 (amino acids 225-541) is N-terminally tagged with 6 histidines and a subsequent Tabacco Etch Virus (TEV) protease cleavage site. It is purified by immobilized metal affinity chromatography (IMAC) via a nickel nitrilotriacetic acid (Ni-NTA) resin (Amersham Biosciences, Freiburg, Germany). Shp-2 enzyme activity was assessed by measuring the absorption generated by the dephosphorylation of 4-nitrophenylphosphate (pNPP) yielding the yellow product 4-nitrophenol (pNP). The assay is carried out in 96-well microtiter plates. The assay buffer contains a final concentration of 25 mM Tris (pH 7.0), 50 mM NaCl, 0.01% Brij35, 10% Glycerol, 1 mM dithiothreitol (DTT) and 25 nM Shp-2, the final assay volume is 100 µl. Compounds are dissolved in dimethylsulfoxide (DMSO), and assays are carried out at a final concentration of 1% DMSO. The reaction is started by adding pNPP to a final concentration of 10 mM and incubated at 30° C. The absorption at 405 nm (A405) is monitored for 60 min in 1 min intervals. A405 is plotted versus time, and the slope in the linear part of the curve is determined (mOD/min). For calculation of the Ki values an extinction coefficient ε of 8200 OD M-1 cm$^{-1}$ (pH 7.0) for 4-nitrophenol is used.

Determination of $IC_{50}$-Values:

Every measurement of the velocity (in mOD/min) of a sample x (SMx) is performed in triplicate and subsequently averaged. A blank control (BL) is determined in at least three separate microtiter wells without phosphatase. As positive control (PC) serves a reaction with phosphatase but without inhibitor in at least three wells. BL and PC are also averaged over all measured wells, respectively. The percentage of signal (% Sig) is determined by the formula % Sig=(SMx−BL/PC−BL)*100%

Afterwards, % Sig is plotted via concentration of the inhibitor (in micromol/liter, logarithmical scale). The resulting curve is fitted to a sigmoidal form with Origin version 6.0 (Microcal Software Inc., Northampton, USA), and the IC50 value can be determined from the fitted curve as the concentration (in micromol/liter) at which the inhibitor reaches half-inhibitory effect (50% signal).

Example 2

HGF/SF Scattering Assay to Measure the Metastatic Potential of Epithelial Cells

Madin-Darby Canine Kidney (MDCK) epithelial cells are seeded at 0.02×10E6 cells/ml (100 µl/well) in a 96 well microtiter plate in Dulbecco's Modified Eagele Medium (DMEM, Invitrogen, Karlsruhe, Germany) supplemented with 10% fetal bovine serum (FBS, Sigma-Aldrich, Munich, Germany) and incubated over night at 37° C. in an humid atmosphere containing 5% carbon dioxide (CO2.) Hepatocyte growth factor/scatter factor (HGF/SF) was expressed in Sf9 insect cells and purified via heparin affinity chromatography. Medium is exchanged against DMEM/10% FBS plus 10 ng/ml HGF/SF plus 5 to 50 µM compound (final DMSO concentration less than 1%). The cells are incubated for 20 h at 37° C./5% CO2 and analyzed under the microscope (Axiovert 135, Carl Zeiss A G, Oberkochen, Germany) for scattering activity. Pictures are taken with a digital camera (ProgRes 3012mF, Jenoptik, Jena, Germany).

Example 3

HGF/SF Phosphorylation Assay

MDCK cells are seeded at 0.15×10E6 cells/ml (1 ml/well) in a 12 well microtiter plate in DMEM/10% FBS and incubated over night at 37° C./5% CO2. Medium is exchanged against DMEM/1% FBS plus 5, 10 or 20 µM (final concentration) compound, and the cells are incubated for 16 h at 37° C./5% CO2. Medium is exchanged against DMEM (without serum) plus 5, 10 or 20 µM compound (final DMSO concentration less than 1%), and the cells are incubated for 2 h at 37° C./5% CO2. Medium is exchanged against DMEM (without serum) plus 5, 10 or 20 µM compound (final DMSO concentration less than 1%) plus 10 ng/ml HGF/SF, and the cells are incubated for 6 h at 37° C./5% CO2. After the indicated time points (0, 5, 15, 60, 120, 360 min) medium is removed, cells are washed once with 1 ml PBS buffer (=137 mM sodium chloride, 3 mM potassium chloride, 1.5 mM potassium dihydrogenphosphate, 8.2 mM disodium hydrogenphosphate, pH 7.4) per well and lysed for 30 min in 200 µl RIPA buffer (=10 mM Tris pH 7.0, 150 mM sodium chloride, 1 mM ethylendiamintetraacetic acid (EDTA) disodium salt, 1% Triton X100, 10% glycerol, 1 mM sodium fluoride, 1 mM sodium orthovanadate, 1 mM phenylmethylsulfonylfluoride (PMSF)) per well at 4° C. Lysates are centrifuged for 5 min at 14000 rpm at 4° C. 75 µl supernatant is boiled with 25 µl 4×SDS sample buffer for 5 min at 95° C. 25 µl sample is separated by sodiumdodecylsulfate polyacrylamide gel electrophoresis (SDS-PAGE) and transferred to nitrocellulose by Western Blotting. Proteins on the blot are analyzed by antibodies against p42/p44 MAP kinase (Erk1/Erk2) (Cell Signaling Technology, Inc., Beverly, USA) and phospho-Erk1/Erk2 (Cell Signaling Technology, Inc., Beverly, USA).

The binding of the antibodies to the MAP kinases on the nitrocellulose was detected by incubation with secondary goat-anti-rabbit-antibodies coupled to horse radish peroxidase (Jackson ImmunoResearch Laboratories, Soham, UK) and subsequent reaction with ECL reagents (Western Lightning™, PerkinElmer Life Sciences, Inc. Boston, USA) and X-ray film exposure (X-OMAT™, Kodak GmbH, Stuttgart, Germany). The intensity of the Western Blot signals was quantified by the imaging software TINA version 2.08e (raytest Isotopenmessgeräte GmbH, Straubenhardt, Germany)."

Example 4

Cell Proliferation Assay (MTT Assay)

Human cancer cell lines MDAMB-435 (melanoma), HCT-116 (colon carcinoma), HCT-15 (colon carcinoma), PC-3 (prostate cancer) HT-29 (colon carcinoma) and NCl-H661 (lung carcinom) were obtained from ATCC/LGC Promochem (Wesel, Germany) All cell lines except HT-29 were maintained n RPMI 1640 medium (Invitrogen, Karlsruhe, Germany) supplemented with 10% FBS. HT-29 cells were maintained in DMEM supplemented with 10% FBS. Compounds were dissolved in DMSO to make a stock of 10 mM. The cells were seeded at a density of 0.01×10E6 cells/ml in 100l medium in a 96 well microtiter plate 24 hr before compound treatment. The cells were then treated with different concentrations of compound in 100 µl of medium and were incubated at 37° C. with 5% $CO_2$ for 6 days (the maximum final concentration of DMSO in medium was 0.5%). To set up a standard curve, the corresponding cells were seeded at a series of different densities in 100 µl of medium per well in a 96-well microtiter plate at the end of the incubation periods of the experimental cells. 10 µl of 5 mg/ml solution of methylthiazolyldiphenyltetrazolium bromide (MTT; Sigma-Aldrich, Munich, Germany) was added to each well, and the cells were incubated at 37° C. for 4 h. 100 µl of acidic isopropanol (0.04 M hydrochloric acid in isopropanol) was then added to each well to dissolve the blue complexes. Finally, the absorbance of the converted dye was measured at a wavelength of 550 nm with background subtraction at 630 nm. The numbers of living cells at the time of assay were read from the standard curve. Each condition was done in triplicate, and the data were shown as mean ±standard error of the mean (SEM) from at least 3 independent experiments.

Example 5

Colony Formation Assay (Soft Agar Assay)

Soft agar colony formation assay was performed in 6 well microtiter plates. Each well contained 1.5 ml of 0.6% agar in complete medium as the bottom layer 15 ml of 0.3% agar in complete medium, 1×10E4 cells and various concentration of compound as the feeder layer and 1 ml complete medium supplemented with various concentration of compound as the top layer. Cells were maintained at 37° C. 5% $CO_2$ for 3-4 weeks The top-layered medium was changed every 7 days. At the end of the experiment, the colonies were stained with p-iodonitrotetrazolium violet and viewed under an inverted microscope (Zeiss Axiovert 135, Carl Zeiss A G, Oberkochen, Germany) at 100× magnification. Ten fields were randomly chosen for each well, the area occupied by colonies (both numbers and sizes of colonies were taken into account) was estimated as a pixel value of stained colonies using a digital camera (ProgRes 3012mF, Jenoptik, Jena, Germany) and graphic software (Adobe Photoshop V7.0, Adobe Systems GmbH, Munich, Germany).

Example 6

HGF/SF Phosphorylation Assay

Typically, human tumor cells (e.g. NCI-H661) were seeded at 0.25×10E6 cells/ml (1 ml/well) in a 6 well microtiter plate in RPMI/10% FBS and incubated over night at 37° C./5% CO2. Medium is exchanged against RPMI/1% FBS plus 5, 10 or 20 µM (final concentration) compound, and the cells were incubated for 20 h at 37° C./5% CO2. Medium was exchanged against RPMI (without serum) plus 5, 10 or 20 µM compound (final DMSO concentration less than 1%), and the cells were incubated for 4 h at 37° C./5% CO2. Medium was exchanged against DMEM (without serum) plus 5, 10 or 20 µM compound (final DMSO concentration less than 1%) plus 10 ng/ml HGF/SF, and the cells were incubated for 4 h at 37° C./5% CO2. After the indicated time points (0, 5, 15, 60, 120, 240 min) medium was removed, cells were washed once with 1 ml PBS buffer (=137 mM sodium chloride, 3 mM potassium chloride, 1.5 mM potassium dihydrogenphosphate, 8.2 mM disodium hydrogenphosphate, pH 7.4) per well and lysed for 30 min in 200 µl RIPA buffer (=10 mM Tris pH 7.0, 150 mM sodium chloride, 1 mM ethylendiamintetraacetic acid (EDTA) disodium salt, 1% Triton X100, 10% glycerol, 1 mM sodium fluoride, 1 mM sodium orthovanadate, 1 mM phenylmethylsulfonylfluoride (PMSF)) per well at 4° C. Lysates were centrifuged for 5 min at 14000 rpm at 4° C. 75 µl supernatant was boiled with 25 µl 4×SDS sample buffer for 5 min at 95° C. 25 µl sample was separated by sodiumdodecylsulfate polyacrylamide gel electrophoresis (SDS-PAGE) and transferred to nitrocellulose by Western Blotting. Proteins on the blot were analyzed by antibodies against p42/p44 MAP kinase (Erk1/Erk2) (Cell Signaling Technology, Inc., Beverly, USA) and phospho-Erk1/Erk2 (Cell Signaling, Technology, Inc., Beverly, USA). The binding of the antibodies to the MAP kinases on the nitrocellulose was detected by incubation with secondary goat-anti-rabbit-antibodies coupled to horse radish peroxidase (Jackson ImmunoResearch Laboratories, Soham, UK) and subsequent reaction with ECL reagents (Western Lightning™, PerkinElmer Life Sciences, Inc. Boston, USA) and X-ray film exposure (X-OMAT™, Kodak GmbH, Stuttgart, Germany).

Example 7

Synthesis of Compound II-1

Methyl 2-(triphenylphosphoranylidene)-acetate (502 mg, 15 mmol) was dissolved in dry dichloromethane (5 ml). A mixture of 4-nitrobenzoic acid (301 mg, 18 mmol), MSNT (533 mg, 18 mmol) and lutidine (182 mg, 17 mmol) in dry dichloromethane (5 ml) was added. The crude product methyl 3-(4-nitrophenyl)-3-oxo-2-triphenylphosphoranylidene-propanoate was purified by flash chromatography over silica gel employing ethyl acetate/hexane (80:20, v/v) as eluent.

Dimethyldioxirane (1.2 mmol) was added to a solution of the purified product (193 mg, 0.4 mmol) in 2 ml dichloromethane. The crude product was purified by flash chromatography over silica gel employing ethyl acetate/hexane (40:60, v/v) as eluent.

The purified product methyl 2,2-dihydroxy-3-(4-nitrophenyl)-3-oxo-propanoate (95 mg, 0.4 mmol) was dissolved in ethanol (10 ml), and 4-hydrazinylbenzenesulfonic acid hemihydrate 99 mg, 0.5 mmol) and hydrochloric acid (37%, 0.1 ml) was added. After the reaction time (16 h) the solvent was removed in vacuo. The residue contained methyl 3-(4-nitrophenyl)-3-oxo-2-(2-(4-sulfophenyl)hydrazono)-propanoate.

This crude product (81 mg, 0.2 mmol) was dissolved in ethanol (10 ml), and phenylhydrazine (26 mg, 0.24 mmol) and hydrochloric acid (37%, 0.1 ml) were added. 53 mg of the product 4-((1,5-dihydro-3-(4-nitrophenyl)-5-oxo-1-phenyl-4H-pyrazol-4-ylidene)-hydrazino)-benzenesulfonic acid were isolated by filtration as an orange solid (yield 54%).

ESI/MS: m/z 466.0 [M+H$^+$]

$^1$H-NMR (DMSO-d$_6$, 300 MHz): δ=8.49-8.40 (m, 4H, NO$_2$-Ph), 8.06-8.03 (d, J=9 Hz, 2H, SO$_3$H-Ph), 7.74-7.64 (m, 4H, SO$_3$H-Ph and Ph), 7.54-7.49 (m, 2H, Ph), 7.16-7.10 (m, 1H, Ph).

$^{13}$C-NMR (DMSO-d$_6$, 75 MHz): δ=146.38, 143.90, 135.95, 129.06, 128.07, 126.95, 124.02, 120.46, 118.52, 116.43.

Example 8

Synthesis of Compound II-6

Methyl 2-(triphenylphosphoranylidene)-acetate (502 mg, 15 mmol) was dissolved in dry dichloromethane (5 ml). A mixture of 4-fluorobenzoic acid (252 mg, 18 mmol), MSNT (533 mg, 18 mmol) and lutidine (182 mg, 17 mmol) in dry dichloromethane (5 ml) was added. The crude product methyl 3-(4-fluorophenyl)-3-oxo-2-triphenylphosphoranylidene-propanoate was purified by flash chromatography over silica gel employing ethyl acetate/hexane (50:50, v/v) as eluent.

Dimethyldioxirane (1.2 mmol) was added to a solution of the purified product (182 mg, 0.4 mmol) in 2 ml dichloromethane. The crude product was purified by flash chromatography over silica gel with ethyl acetate/hexane (33:66, v/v) as eluent.

The purified product methyl 2,2-dihydroxy-3-(4-fluorophenyl)-3-oxo-propanoate (84 mg, 0.4 mmol) was dissolved in ethanol (10 ml), and 4-hydrazinylbenzenesulfonic acid hemihydrate (99 mg, 0.5 mmol) and hydrochloric acid (37%, 0.1 ml) were added. After the reaction time (16 h) the solvent was removed in vacuo. The residue contained methyl 3-(4-fluorophenyl)-3-oxo-2-(2-(4-sulfophenyl)hydrazono)-propanoate. This crude product (137 mg, 0.36 mmol) was dissolved in ethanol (10 ml), and phenylhydrazine (46 mg, 0.43 mmol) and hydrochloric acid (37%, 0.1 ml) were added. 126 mg of the product 4-((1,5-dihydro-3-(4-fluorophenyl)-5-oxo-1-phenyl-4H-pyrazol-4-ylidene)-hydrazino)-benzenesulfonic acid were isolated by filtration as a red solid (yield 80%).

ESI/MS: m/z 439.2 [M+H$^+$]

$^1$H-NMR (DMSO-d$_6$, 300 MHz): δ=8.26-8.21 (m, 2H), 8.03-8.00 (m, 2H), 7.71-7.58 (m, 5H), 7.33-7.24 (m, 3H), 6.94-6.92 (m, 1H).

$^{13}$C-NMR (DMSO-d$_6$, 75 MHz): δ=164.67, 161.39, 156.89, 145.31, 140.97, 137.72, 129.06, 129.03, 127.05, 126.48, 126.44, 125.31, 121.64, 118.27, 114.33.

Example 9

Synthesis of Compound II-7

Methyl 2-(triphenylphosphoranylidene)-acetate (502 mg, 15 mmol) was dissolved in dry dichloromethane (5 ml). A mixture of 3-nitrobenzoic acid (301 mg, 18 mmol), MSNT (533 mg, 18 mmol) and lutidine (182 mg, 17 mmol) in dry dichloromethane (5 ml) were added. The crude product was purified by flash chromatography over silica employing ethyl acetate/hexane (80:20, v/v) as eluent.

Dimethyldioxirane (1.2 mmol) was added to a solution of the purified product methyl 3-(3-nitrophenyl)-3-oxo-2-triphenyl phosphoranylidene-propanoate (193 mg, 0.4 mmol) in dichloromethane (2 ml). The crude product was purified by flash chromatography over silica gel with ethyl acetate/hexane (50:50, v/v) as eluent.

The purified product methyl 2,2-dihydroxy-3-(3-nitrophenyl)-3-oxo-propanoate (95 mg, 0.4 mmol) was dissolved in ethanol (10 ml), and 4-hydrazinylbenzenesulfonic acid hemihydrate (99 mg, 0.5 mmol) and hydrochloric acid (37%, 0.1 ml) were added. After the reaction time (16 h) the solvent was removed in vacuo. The residue contained methyl 3-(3-nitrophenyl)-3-oxo-2-(2-(4-sulfophenyl)hydrazono)-propanoate.

This crude product (142 mg, 0.35 mmol) was dissolved in ethanol (10 ml), and phenylhydrazine (45 mg, 0.42 mmol) and hydrochloric acid (36-38%, 0.1 ml) were added. 61 mg of the product 4-((1,5-dihydro-3-(3-nitrophenyl)-5-oxo-1-phenyl-4H-pyrazol-4-ylidene)-hydrazino)-benzenesulfonic acid were isolated by filtration as an orange solid (yield 37%).

ESI/MS: m/z 466.0 [M+H$^+$]

$^1$H-NMR (DMSO-d$_6$, 300 MHz): δ=8.66-8.63 (m, 1H, NO$_2$-Ph), 8.21-8.18 (m, 3H, NO$_2$-Ph), 7.77-7.60 (m, 6H, SO$_3$H-Ph und Ph), 7.43-7.38 (m, 2H, Ph), 7.14-7.09 (m, 1H, Ph).

$^{13}$C-NMR (DMSO-d$_6$, 75 MHz): δ=185.45, 155.38, 147.75, 145.40, 144.26, 140.29, 135.86, 132.93, 129.48, 128.41, 126.03, 123.36, 122.54, 122.13, 119.61, 118.48.

Example 10

Synthesis of Compound II-8

The crude product methyl 3-(4-nitrophenyl)-3-oxo-2-(2-(4-sulfophenyl)hydrazono)-propanoate (102 mg, 0.25 mmol) (synthesized as described for 11-1) was dissolved in ethanol (10 ml), and 4-trifluormethylphenylhydrazine (53 mg, 0.3 mmol) and hydrochloric acid (37%, 0.1 ml) were added. 44 mg of the product 4-((1,5-dihydro-3-(4-nitrophenyl)-5-oxo-1-(4-trifluormethylphenyl)-4H-pyrazol-4-ylidene)-hydrazino)-benzenesulfonic acid were isolated by filtration as an orange solid (yield 34%).

ESI/MS: m/z 534.2 [M+H$^+$]

$^1$H-NMR (DMSO-d$_6$, 300 MHz): δ=8.47-8.40 (m, 4H), 8.27-8.24 (m, 2H), 7.73-7.64 (m, 6H).

$^{13}$C-NMR (DMSO-d$_6$, 75 MHz): δ=160.25, 157.11, 148.71, 147.86, 146.53, 144.68, 140.82, 135.69, 128.20, 127.06, 126.37, 125.52, 124.06, 121.47, 118.07.

Example 11

Synthesis of Compound II-9

Methyl 2-(triphenylphosphoranylidene)-acetate (502 mg, 15 mmol) was dissolved in dry dichloromethane (5 ml). A mixture of 4-chlorobenzoic acid (282 mg, 18 mmol), MSNT (533 mg, 18 mmol) and lutidine (182 mg, 17 mmol) in dry dichloromethane (5 ml) was added. The crude product was purified by flash chromatography over silica gel employing ethyl acetate/hexane (40:60, v/v) as eluent.

Dimethyldioxirane (1.2 mmol) was added to a solution of the purified product methyl 3-(4-chlorophenyl)-3-oxo-2-triphenylphosphoranylidene-propanoate (189 mg, 0.4 mmol) in 2 ml dichloromethane. The crude product was purified by flash chromatography over silica gel with ethyl acetate/hexane (30:70, v/v) as eluent. The purified product methyl 2,2-dihydroxy-3-(4-chlorophenyl)-3-oxo-propanoate (104 mg, 0.46 mmol) was dissolved in ethanol (10 ml), and 4-hydrazinylbenzenesulfonic acid hemihydrate (108 mg, 0.55 mmol) and hydrochloric acid (37%, 0.1 ml) were added. After the reaction time (16 h) the solvent was removed in vacuo. The residue contained methyl 3-(4-chlorophenyl)-3-oxo-2-(2-(4-sulfophenyl)hydrazono)-propanoate. This crude product (159 mg, 0.4 mmol) was dissolved in ethanol (10 ml), and phenylhydrazine (52 mg, 0.48 mmol) and hydrochloric acid (37%, 0.1 ml) were added. 34 mg of the product 4-((1,5-dihydro-3-(4-chlorophenyl)-5-oxo-1-phenyl-4H-pyrazol-4-ylidene)-hydrazino)-benzenesulfonic acid were isolated by filtration as a brown solid (yield 21%).

ESI/MS: m/z 455.0 [M+H$^+$]

$^1$H-NMR (DMSO-d$_6$, 300 MHz): δ=8.24-8.17 (m, 4H), 7.61-7.48 (m, 6H), 7.40-7.35 (m, 2H, Ph), 7.11-7.06 (m, 1H, Ph).

$^{13}$C-NMR (DMSO-d$_6$, 75 MHz): δ=155.52, 145.21, 140.50, 133.22, 129.18, 128.31, 127.92, 126.00, 119.43, 118.25.

Example 12

Synthesis of Compound II-10

The crude product methyl 3-(4-nitrophenyl)-3-oxo-2-(2-(4-sulfophenyl)hydrazono)-propanoate (200 mg, 0.49 mmol) (synthesized as described for II -1) was dissolved in ethanol (10 ml), and 4-hydrazinobenzoic acid (90 mg, 0.59 mmol) and hydrochloric acid (37%, 0.2 ml) were added. The product 4-((1,5-dihydro-3-(4-nitrophenyl)-5-oxo-1-(4-ethoxycarbonyl phenyl)-4H-pyrazol-4-ylidene)-hydrazino)-benzenesulfonic acid was isolated by filtration as an orange solid (yield 54%).

ESI/MS: m/z 538.2 [M+H$^+$]

$^1$H-NMR (DMSO-d$_6$, 300 MHz): δ=8.45-8.38 (m, 4H, COOR-Ph), 8.18-8.04 (m, 4H, NO$_2$-Ph), 7.73-7.65 (m, 4H, SO$_3$H-Ph), 4.16 (m, 2H, CH$_2$), 1.33 (m, 1H, CH$_3$).

$^{13}$C-NMR (DMSO-d$_6$, 75 MHz): δ=165.06, 157.11, 147.84, 146.48, 144.63, 141.23, 140.83, 135.70, 130.37, 128.18, 127.07, 126.24, 126.03, 117.45, 60.70, 14.17.

Example 13

Synthesis of Compound II-11

The crude product methyl 3-(4-nitrophenyl)-3-oxo-2-(2-(4-sulfophenyl)hydrazono)-propanoate (200 mg, 0.49 mmol) (synthesized as described for 11-1) was dissolved in ethanol (10 ml), and 4-fluorophenylhydrazine (96 mg, 0.59 mmol) and hydrochloric acid (37%, 0.2 ml) were added. The product 4-((1,5-dihydro-3-(4-nitrophenyl)-5-oxo-1-(4-fluorophenyl)-4H-pyrazol-4-ylidene)-hydrazino)-benzenesulfonic acid was isolated by filtration as a brown solid (yield 82%).

ESI/MS: m/z 483.9 [M+H$^+$]

$^1$H-NMR (DMSO-d$_6$, 300 MHz): δ=8.49-8.38 (m, 4H, F-Ph, NO$_2$-Ph), 8.03-7.99 (m, 2H, NO$_2$-Ph), 7.76-7.64 (m, 4H, SO$_3$H-Ph), 7.38-7.33 (m, 2H, F-Ph).

$^{13}$C-NMR (DMSO-d$_6$, 75 MHz): δ=147.72, 143.78, 140.86, 137.48, 135.90, 128.03, 127.07, 126.23, 124.07, 120.64, 117.45, 116.19.

Example 14

Synthesis of Compound II-12

4-((1,5-dihydro-3-(4-nitrophenyl)-5-oxo-1-(4-ethoxycarbonyl phenyl)-4H-pyrazol-4-ylidene)-hydrazino)-benzenesulfonic acid (53 mg, 0.1 mmol) (II-10) was dissolved in water (2 ml) and ethanol (4 ml). Potassium hydroxide (19 mg, 0.35 mmol) was added. The reaction mixture was boiled at 110° C. for 4 h under reflux. Subsequently, hydrochloric acid (37%, 0.3 ml) was dropped carefully to the reaction mixture. The precipitate that was formed contained 4-((1,5-dihydro-3-(4-nitrophenyl)-5-oxo-1-(4-carboxyphenyl)-4H-pyrazol-4-ylidene)-hydrazino)-benzenesulfonic acid which was isolated by filtration as a red solid (yield 48%).

ESI/MS: m/z 510.00 [M+H$^+$]

$^1$H-NMR (DMSO-d$_6$, 300 MHz): δ=8.49-8.42 (m, 4H, COOH-Ph), 8.20-8.07 (m, 4H, NO$_2$-Ph), 7.73-7.66 (m, 4H, SO$_3$H-Ph).

$^{13}$C-NMR (DMSO-d$_6$, 75 MHz): δ=166.65, 157.13, 147.85, 144.61, 141.01, 135.77, 128.22, 127.24, 127.06, 126.11, 124.09, 117.50.

FIG. 1 shows structure activity relationship of compounds of formula I. IC50 values (in µM) were determined according to example 1. Inhibition of scattering of MDCK cells was determined according to example 2; "+++" represents complete or nearly complete (90-100%) inhibition, "++" represents intermediate inhibition (50-90%), "+" represents weak inhibition (10-40%), "−" represents very weak or no inhibition (0-10%) of scattering with 15 µM of the indicated compound. Compounds I-3 and I -4 which are not covered from formula (I) of the invention have been investigated for comparison reasons.

FIG. 2 shows structure activity relationship of compounds of formula II. IC50 values (in µM) were determined according to example 1. Inhibition of scattering of MDCK cells was determined according to example 2; "+++" represents complete or nearly complete (90-100%) inhibition, "++" represents intermediate inhibition (50-90%), "+" represents weak inhibition (10-40%), "−" represents very weak or no inhibition (0-10%) of scattering with 15 µM of the indicated compound. Compounds II-4 and 11-5 which are not covered from formula (II) of the invention have been investigated for comparison reasons.

FIG. 3 shows HGF/SF scattering assay. Inhibition of scattering of MDCK cells was carried out according to example 2 with compound I-1 and II-1 of this invention.

FIG. 4 shows HGF/SF phosphorylation assay.

A: Inhibition of phosphorylation of MAP kinases Erk1 and Erk2 was carried out according to example 3 with compound II-1 of this invention. "II-1" indicates concentration of compound II-1 in micromol/liter. "HGF" indicates stimulation of MDCK cells in minutes before lysis. "P-Erk1/2" indicates Western Blot signals with antibody against MAP kinase p44/Erk1 (upper band) or p42/Erk2 (lower band) phosphorylated on threonine 202 and tyrosine 204. "Erk1/2" indicates Western Blot signals with antibody against MAP kinase p44/Erk1 (upper band) or p42/Erk2 (lower band) either phosphorylated or unphosphorylated.

B: Intensity of phosphorylation signals of Erk1 ("P-Erk1") was quantified relative to signal of Erk1 ("Erk1") and is expressed as "P-Erk1/Erk1" in %. Concentration of compound II-1 is indicated in white (0 µM), light grey (5 µM), grey (10 μM) and dark grey (20 μM). "HGF" is indicated as above. Note that sustained MAP kinase phosphorylation is inhibited by compound II-1 in a dose dependant manner.

FIG. 5 shows MTT assay with compound II-1. Inhibition of growth of various human tumor cell lines (MDA-MB-435, HCT-116, HCT-15, HT-29, PC-3 and NCI-H661, as indicated below) was carried out according to example 4 with compound II-1 of this invention. Concentrations of compound II-1 are indicated in white (0 μM) and black (30 μM), respectively.

FIG. 6 shows soft agar assay with compound II-1. Inhibition of colony formation of various human tumor cell lines (MDA-MB-435, HCT-116, HCT-15, HT-2 and PC-3, as indicated below) was carried out according to example 5 with compound II-1 of this invention.

A. Representative microscope pictures of the colonies were taken typically after 3 weeks according to example 5. Concentrations of compound II-1 are indicated on the left.

B. Quantification of colony size (in relative pixel values) was performed according to example 5. Concentrations of compound II-1 are indicated in white (0 μM), grey (15 μM) and black (30 μM), respectively.

FIG. 7 shows HGF/SF phosphorylation assay with tumor cell line NCI-H661 treated with compound II-1. Inhibition of phosphorylation of MAP kinases Erk1 and Erk2 was carried out according to example 6 with compound II-1 of this invention. "II-1" indicates concentration of compound II-1 in micromol/liter. "HGF" indicates stimulation of NCI-H661 cells in minutes before lysis. "P-Erk1/2" indicates Western Blot signals with antibody against MAP kinase p44/Erk1 (upper band) or p42/Erk2 (lower band) phosphorylated on threonine 202 and tyrosine 204. "Erk1/2" indicates Western Blot signals with antibody against MAP kinase p44/Erk1 (upper band) or p42/Erk2 (lower band) either phosphorylated or unphosphorylated. Note that sustained MAP kinase phosphorylation in NCI-H661 cells (containing the putative activating mutation N58S in the SHP2/PTPN11 gene; see Bentires-Alj, M. et al., Cancer Res. 64, 8816-8820, 2004) is inhibited by compound II-1 in a dose dependant manner.

LITERATURE

Bennett, A. M., Hausdorff, S. F., O'Reilly, A. M., Freeman, R. M., and Neel, B. G. (1996). Multiple requirements for SHPTP2 in epidermal growth factor-mediated cell cycle progression. Mol Cell Biol 16, 1189-1202.

Birchmeier, C., Birchmeier, W., Gherardi, E., and Vande Woude, G. F. (2003). Met, metastasis, motility and more. Nat Rev Mol Cell Biol 4, 915-925.

Huijsduijnen, R. H. v., Sauer, W. H., Bombrun, A., and Swinnen, D. (2004). Prospects for inhibitors of protein tyrosine phosphatase 1B as antidiabetic drugs. J Med Chem 47, 4142-4146.

Jeffers, M., Fiscella, M., Webb, C. P., Anver, M., Koochekpour, S., and Vande Woude, G. F. (1998). The mutationally activated Met receptor mediates motility and metastasis. Proc Natl Acad Sci USA 95, 14417-14422.

Kodama, A., Matozaki, T., Fukuhara, A., Kikyo, M., Ichihashi, M., and Takai, Y. (2000). Involvement of an SHP-2-Rho small G protein pathway in hepatocyte growth factor/scatter factor-induced cell scattering. Mol Biol Cell 11, 2565-2575.

Morotti, A., Mila, S., Accornero, P., Tagliabue, E., and Ponzetto, C. (2002). K252a inhibits the oncogenic properties of Met, the HGF receptor. Oncogene 21, 4885-4893.

Schaeper, U., Gehring, N. H., Fuchs, K. P., Sachs, M., Kempkes, B., and Birchmeier, W. (2000). Coupling of Gab1 to c-Met, Grb2, and Shp2 mediates biological responses. J Cell Biol 149, 1419-1432.

Webb, C. P., Hose, C. D., Koochekpour, S., Jeffers, M., Oskarsson, M., Sausville, E., Monks, A., and Vande Woude, G. F. (2000). The geldanamycins are potent inhibitors of the hepatocyte growth factor/scatter factor-met-urokinase plasminogen activator-plasmin proteolytic network. Cancer Res 60, 342-349.

Bentires-Alj, M., Paez, J. G., David, F. S., Keilhack, H., Halmos, B., Naoki, K., Maris, J. M., Richardson, A., Bardelli, A., Sugarbaker, D. J., et al. (2004). Activating mutations of the noonan syndrome-associated SHP2/PTPN11 gene in human solid tumors and adult acute myelogenous leukemia. Cancer Res 64, 8816-8820.

The invention claimed is:

1. An acid of formula (II)

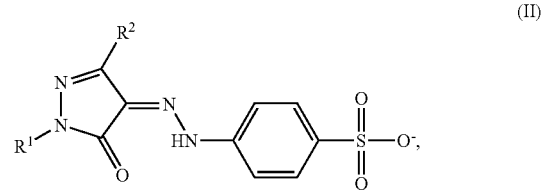

or a pharmaceutically acceptable salt thereof,
wherein
$R^1$ is unsubstituted aryl or heteroaryl or aryl or heteroaryl substituted with alkyl, alkylamino, halogen, haloalkyl, carboxy, alkoxycarbonyl, hydroxy, N-morpholino, N-morpholinoalkyl, N-morpholinocarbonyl, N-methyl-N-piperazinyl, N-methyl-N-piperazinylalkyl, N-methyl-N-piperazinylcarbonyl or sulfo, and
$R^2$ is phenyl substituted with a nitro, halogen, haloalkyl, carboxy, alkoxycarbonyl, hydroxy or sulfo group, with exclusion of 4-((1,5-dihydro-3-(4-nitrophenyl)-5-oxo-1-phenyl-4H-pyrazol-4-ylidene)-hydrazino)-benzenesulfonic acid and 4,4'-(4,5-dihydro-5-oxo-((4-sulfophenyl)-hydrazono)-1H-pyrazole-1,3-diyl)-bisbenzenesulfonic acid.

2. The acid according to claim 1, wherein aryl is phenyl and heteroaryl is thiazolyl, pyridinyl, pyrimidinyl, imidazolyl or triazolyl, or a pharmaceutically acceptable salt thereof.

3. The acid according to claim 1, wherein $R^1$ is phenyl or phenyl substituted with halogen, haloalkyl, carboxy, alkoxycarbonyl, hydroxy, N-morpholino, N-morpholinoalkyl, N-morpholinocarbonyl, N-methyl-N-piperazinyl, N-methyl-N-piperazinylalkyl, N-methyl-N-piperazinylcarbonyl or sulfo, or a pharmaceutically acceptable salt thereof.

4. The acid according to claim 1, wherein the substituents in the phenyl moiety are in 3- or 4-position, or a pharmaceutically acceptable salt thereof.

5. The acid according to claim 1, wherein $R^1$ is phenyl, 4-halophenyl, 4-trifluoromethylphenyl, 4-carboxyphenyl or 4-ethoxycarbonylphenyl, or a pharmaceutically acceptable salt thereof.

6. The acid according to claim 1, wherein $R^2$ is 4-nitrophenyl or 4-halophenyl, or a pharmaceutically acceptable salt thereof.

7. The acid according to claim 1, wherein aryl is phenyl and heteroaryl is 1,2,4-triazolyl, or a pharmaceutically acceptable salt thereof.

8. The acid according to claim 1, wherein the substituents in the phenyl moiety are in 4-position, or a pharmaceutically acceptable salt thereof.

9. The acid according to claim 1, wherein $R^1$ is 4-fluorophenyl, or a pharmaceutically acceptable salt thereof.

10. A pharmaceutical composition comprising a compound of claim 1 and a pharmaceutically acceptable carrier.

11. The pharmaceutical composition comprising a compound of claim 2 and a pharmaceutically acceptable carrier.

12. The pharmaceutical composition comprising a compound of claim 3 and a pharmaceutically acceptable carrier.

13. The pharmaceutical composition comprising a compound of claim 4 and a pharmaceutically acceptable carrier.

14. The pharmaceutical composition comprising a compound of claim 5 and a pharmaceutically acceptable carrier.

15. The pharmaceutical composition comprising a compound of claim 6 and a pharmaceutically acceptable carrier.

16. The pharmaceutical composition comprising a compound of claim 7 and a pharmaceutically acceptable carrier.

17. The pharmaceutical composition comprising a compound of claim 8 and a pharmaceutically acceptable carrier.

18. The pharmaceutical composition comprising a compound of claim 9 and a pharmaceutically acceptable carrier.

* * * * *